(12) United States Patent
Funakubo

(10) Patent No.: US 9,962,143 B2
(45) Date of Patent: May 8, 2018

(54) MEDICAL DIAGNOSIS APPARATUS, ULTRASOUND OBSERVATION SYSTEM, METHOD FOR OPERATING MEDICAL DIAGNOSIS APPARATUS, AND COMPUTER-READABLE RECORDING MEDIUM

(71) Applicant: OLYMPUS CORPORATION, Tokyo (JP)

(72) Inventor: Sho Funakubo, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/426,608

(22) Filed: Feb. 7, 2017

(65) Prior Publication Data

US 2017/0143310 A1 May 25, 2017

Related U.S. Application Data

(63) Continuation of application No. PCT/JP2016/062223, filed on Apr. 18, 2016.

(30) Foreign Application Priority Data

Apr. 30, 2015 (JP) .................................. 2015-093304

(51) Int. Cl.
  *A61B 8/08* (2006.01)
  *A61B 8/14* (2006.01)
  *A61B 8/00* (2006.01)
(52) U.S. Cl.
  CPC .............. *A61B 8/5207* (2013.01); *A61B 8/14* (2013.01); *A61B 8/4483* (2013.01); *A61B 8/461* (2013.01); *A61B 8/467* (2013.01); *A61B 8/54* (2013.01)

(58) Field of Classification Search
  CPC ........ A61B 8/5207; A61B 8/4483; A61B 8/54; A61B 8/467; A61B 8/461; A61B 8/14
  See application file for complete search history.

(56) References Cited

U.S. PATENT DOCUMENTS 9,241,113 B2 * 1/2016 Lee ...................... H04N 5/2624
2014/0114190 A1 * 4/2014 Chiang ................. G06F 3/0488
  600/440

(Continued)

FOREIGN PATENT DOCUMENTS

JP  2004-078977 A  3/2004
JP  2010-274049 A  12/2010

(Continued)

OTHER PUBLICATIONS

International Search Report dated Jun. 7, 2016 issued in PCT/JP2016/062223.

*Primary Examiner* — Andrew Sasinowski
(74) *Attorney, Agent, or Firm* — Scully, Scott, Murphy & Presser, P.C.

(57) ABSTRACT

A medical diagnosis apparatus obtains a signal for generating an image of an observation target and causes an external display device to display an observation image based on the obtained signal to perform diagnosis. The medical diagnosis apparatus includes: a detection unit configured to detect a shape and spatial position of a finger of a practitioner; an executable command selection unit configured to select one or more commands executable by the medical diagnosis apparatus in accordance with the shape and the spatial position of the finger of the practitioner; a command image generation unit configured to generate a command image corresponding to the one or more commands and to generate a finger shape image indicating the shape of the finger of the practitioner; and a display image generation unit configured (Continued)

to generate a display image using the command image, the finger shape image, and the observation image.

15 Claims, 12 Drawing Sheets

(56) References Cited

U.S. PATENT DOCUMENTS

| | | | | |
|---|---|---|---|---|
| 2014/0121524 A1* | 5/2014 | Chiang | ................ | A61B 8/5207 |
| | | | | 600/459 |
| 2016/0004330 A1* | 1/2016 | Sundaran Baby Sarojam | ................ | A61B 8/461 |
| | | | | 345/157 |
| 2016/0007965 A1* | 1/2016 | Murphy | .............. | G01S 7/52084 |
| | | | | 345/173 |

FOREIGN PATENT DOCUMENTS

| | | |
|---|---|---|
| JP | 2014-097229 A | 5/2014 |
| WO | WO 2013/148730 A2 | 10/2013 |
| WO | WO 2014/134316 A1 | 9/2014 |

\* cited by examiner

MEDICAL DIAGNOSIS APPARATUS, ULTRASOUND OBSERVATION SYSTEM, METHOD FOR OPERATING MEDICAL DIAGNOSIS APPARATUS, AND COMPUTER-READABLE RECORDING MEDIUM

CROSS REFERENCES TO RELATED APPLICATIONS

This application is a continuation of PCT international application Ser. No. PCT/JP2016/062223, filed on Apr. 18, 2016 which designates the United States, incorporated herein by reference, and which claims the benefit of priority from Japanese Patent Application No. 2015-093304, filed on Apr. 30, 2015, incorporated herein by reference.

BACKGROUND

1. Technical Field

The disclosure relates to a medical diagnosis apparatus for observing an observation target using ultrasound. The disclosure also relates to an ultrasound observation system, a method for operating the medical diagnosis apparatus, and a computer-readable recording medium.

2. Related Art

Ultrasound is applied in some case for observing characteristics of a living tissue or material as an observation target. Specifically, ultrasound transmitted toward the observation target is reflected as an ultrasound echo from the observation target, and predetermined signal processing is performed on the reflected ultrasound echo, whereby information related to characteristics of the observation target is obtained.

Ultrasound diagnosis of a living tissue, or the like, inside the body uses an ultrasound endoscope in which an ultrasound transducer is provided at a distal end of an insertion unit. A practitioner including a doctor inserts an insertion unit into the body and operates an operating unit at hand, whereby the ultrasound transducer obtains an ultrasound echo and diagnosis is performed on the basis of information based on the ultrasound echo (e.g. ultrasound image).

FIG. 16 is a schematic diagram illustrating a configuration of a system that performs conventional ultrasound diagnosis. An ultrasound diagnosis system 500 illustrated in FIG. 16 includes an ultrasound endoscope 501, an image processing apparatus 502, a keyboard 503, an ultrasound image monitor 504, and an endoscope image monitor 505. The ultrasound endoscope 501 includes an insertion unit. An ultrasound transducer and an imaging element are provided on a distal end of the insertion unit. The image processing apparatus 502 generates an image based on an ultrasound echo and an imaging signal obtained by the ultrasound endoscope 501. The keyboard 503 is connected with the image processing apparatus 502 and used to input a signal such as an instruction signal. The ultrasound image monitor 504 displays an image based on the ultrasound echo. The endoscope image monitor 505 displays an image based on the imaging signal. A practitioner S1 inserts an insertion unit of the ultrasound endoscope 501 into a subject S2, inputs an instruction signal via the keyboard 503 and via an operating unit on the ultrasound endoscope 501, and thus performs adjustment of an ultrasound image, specifically, rotation and movement of the image, thereby performing diagnosis.

Due to the layout of an examination room, or the like, the practitioner S1 and the image processing apparatus 502 (keyboard 503) may be separated from each other. Separation of the practitioner S1 from the image processing apparatus 502 (keyboard 503) would reduce operability. To cope with this issue, there is a technique to enable the practitioner to operate while viewing an ultrasound image monitor 504, or the like, even when the practitioner is separated from the apparatus, by detecting the shape of a finger and allocating functions to the shape in performing pointer and clicking operation (for example, refer to JP 2004-78977 A).

SUMMARY

In some embodiments, a medical diagnosis apparatus is configured to obtain a signal for generating an image of an observation target and configured to cause an external display device to display an observation image based on the obtained signal to perform diagnosis. The medical diagnosis apparatus includes: a detection unit configured to detect a shape of a finger of a practitioner and a spatial position of the finger of the practitioner; an executable command selection unit configured to select one or more commands executable by the medical diagnosis apparatus in accordance with the shape and the spatial position of the finger of the practitioner detected by the detection unit; a command image generation unit configured to generate a command image corresponding to the one or more commands selected by the executable command selection unit and to generate a finger shape image indicating the shape of the finger of the practitioner; and a display image generation unit configured to generate a display image using the command image and the finger shape image, generated by the command image generation unit, and the observation image.

In some embodiments, an ultrasound observation system includes: an ultrasound transducer configured to transmit ultrasound to an observation target and to generate an echo signal being an electrical signal converted from an ultrasound echo that is generated from the ultrasound transmitted to the observation target and reflected from the observation target; an imaging unit configured to generate an imaging signal being an electrical signal converted from a received light signal; a display device configured to display a plurality of observation images based on at least one of the echo signal and the imaging signal; a detection unit configured to detect a shape of a finger of a practitioner and a spatial position of the finger of the practitioner; an executable command selection unit configured to select one or more executable commands in accordance with the shape and the spatial position of the finger of the practitioner detected by the detection unit; a command image generation unit configured to generate a command image corresponding to the one or more commands selected by the executable command selection unit and to generate a finger shape image indicating the shape of the finger of the practitioner; and a display image generation unit configured to generate a display image using the command image and the finger shape image generated by the command image generation unit, and the observation image.

In some embodiments, a method for operating a medical diagnosis apparatus is provided. The medical diagnosis apparatus is configured to obtain a signal for generating an image of an observation target and configured to cause an external display device to display an observation image based on the obtained signal to perform diagnosis. The method includes: detecting, by a detection unit, a shape of a finger of a practitioner and a spatial position of the finger of the practitioner; selecting, by an executable command selection unit, one or more commands executable by the medical diagnosis apparatus in accordance with the shape and the spatial position of the finger of the practitioner detected by the detection unit; generating, by a command image generation unit, a command image corresponding to the one or more commands selected by the executable command selection unit, and generating a finger shape image indicating the shape of the finger of the practitioner; and generating, by a display image generation unit, a display image using the command image and the finger shape image generated by the command image generation unit, and the observation image.

In some embodiments, provided is a non-transitory computer-readable recording medium with an executable program stored thereon for operating a medical diagnosis apparatus. The medical diagnosis apparatus is configured to obtain a signal for generating an image of an observation target and configured to cause an external display device to display an observation image based on the obtained signal to perform diagnosis. The program causes the medical diagnosis apparatus to execute: detecting, by a detection unit, a shape of a finger of a practitioner and a spatial position of the finger of the practitioner; selecting, by an executable command selection unit, one or more commands executable by the medical diagnosis apparatus in accordance with the shape and the spatial position of the finger of the practitioner detected by the detection unit; generating, by a command image generation unit, a command image corresponding to the one or more commands selected by the executable command selection unit, and generating a finger shape image indicating the shape of the finger of the practitioner; and generating, by a display image generation unit, a display image using the command image and the finger shape image generated by the command image generation unit, and the observation image.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter, referred to as embodiment(s)) will be described with reference to the attached drawings. The following description will exemplify an ultrasound diagnosis system and an ultrasound endoscope system including a medical diagnosis apparatus that generates an ultrasound image based on an ultrasound echo. The present invention, however, is not limited to these embodiments. The same reference signs are used to designate the same elements throughout the drawings.

First Embodiment

Figure 1:
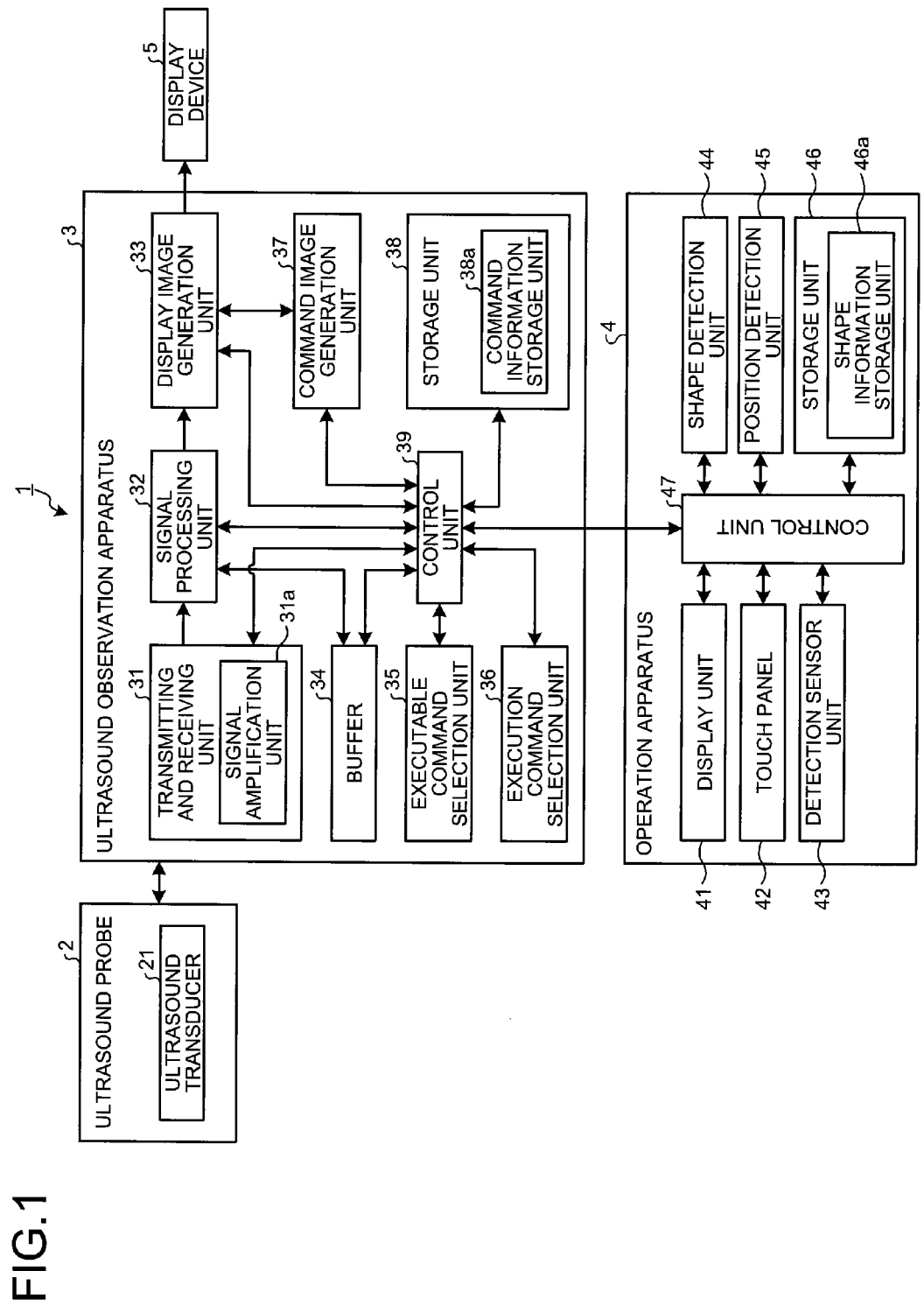
FIG. 1 is a block diagram illustrating a configuration of an ultrasound diagnosis system according to a first embodiment of the present invention.

FIG. 1 is a block diagram illustrating a configuration of an ultrasound diagnosis system according to a first embodiment of the present invention. An ultrasound diagnosis system 1 illustrated in the diagram is an apparatus for observing an observation target using ultrasound and corresponds to a medical diagnosis apparatus according to the present invention.

The ultrasound diagnosis system 1 includes an ultrasound probe 2, an ultrasound observation apparatus 3, an operation apparatus 4, and a display device 5. The ultrasound probe 2 outputs ultrasound and receives a reflected ultrasound echo. The ultrasound observation apparatus 3 generates an individual images based on the ultrasound echoes obtained by the ultrasound probe 2. The operation apparatus 4 is capable of simultaneously receiving a plurality of sets of input instruction information, outputs received information to the ultrasound observation apparatus 3, and operates the ultrasound observation apparatus 3. The display device 5 displays various types of information including the image based on the ultrasound echo generated by the ultrasound observation apparatus 3. The display device 5 includes a display panel formed with liquid crystal, organic electro luminescence (EL), or the like.

The ultrasound probe 2 includes, at its distal end, an ultrasound transducer 21 that outputs an ultrasound pulse to the observation target and receives the ultrasound echo reflected from the observation target.

In a case where the observation target is a living tissue, the ultrasound transducer 21 may take any form of an external probe configured to emit ultrasound from a surface of the living body, a miniature ultrasound probe including a long-shaft insertion unit to be inserted into intraluminal portions such as the gastrointestinal tract, the biliopancreatic duct, and the blood vessel, and an ultrasound endoscope configured to further include an optical system in addition to an intraluminal ultrasound probe. In a case where the form of the ultrasound endoscope is taken from among these, the ultrasound transducer 21 is provided on a distal end side of the insertion unit of the intraluminal ultrasound probe, which is removably connected to the processing apparatus on the proximal end side.

The ultrasound transducer 21 converts an electrical pulse signal received from the ultrasound observation apparatus 3 into an ultrasound pulse (acoustic pulse signal), and converts an ultrasound echo reflected on an external specimen, into an electrical echo signal. The ultrasound transducer 21 may be configured to cause the ultrasound transducer to perform mechanical scan or cause the plurality of ultrasound transducers to perform electronic scan.

The ultrasound observation apparatus 3 includes a transmitting and receiving unit 31, a signal processing unit 32, a display image generation unit 33, a buffer 34, an executable command selection unit 35 (command selection unit), an execution command selection unit 36, a command image generation unit 37, a storage unit 38, and a control unit 39.

The transmitting and receiving unit 31 transmits and receives electrical signals with the ultrasound transducer 21. The transmitting and receiving unit 31 is electrically connected with the ultrasound transducer 21, transmits an electrical pulse signal to the ultrasound transducer 21, and receives an echo signal as an electrical reception signal from the ultrasound transducer 21. Specifically, the transmitting and receiving unit 31 generates an electrical pulse signal on the basis of a preset waveform and transmission timing and transmits the generated pulse signal to the ultrasound transducer 21.

The transmitting and receiving unit 31 includes a signal amplification unit 31a that amplifies an echo signal. The signal amplification unit 31a performs sensitivity time control (STC) correction that amplifies an echo signal having a larger receiving depth by using a higher amplification factor. The transmitting and receiving unit 31 performs processing such as filtering on the echo signal amplified by the signal amplification unit 31a, thereafter, generates digital high-frequency signal, namely, a radio frequency (RF) signal of time domain by performing A/D conversion on the signal, and outputs the generated signal.

The signal processing unit 32 performs signal processing toward the electrical echo signal. Specifically, the signal processing unit 32 generates B-mode image data, as an ultrasound image (observation image) displayed by converting amplitude of an echo signal into luminance. The signal processing unit 32 generates B-mode image data by performing, on a digital signal, signal processing using a known technique, such as a band-pass filter, logarithmic transformation, gain processing, and contrast processing. The B-mode image is a gray-scale image in which values of R (red), G (green) and B (blue), namely, variables when the RGB color system is employed as a color space, match with each other.

The signal processing unit 32 generates B-mode image data by sequentially performing signal processing on a digital RF signal output from the transmitting and receiving unit 31 and outputs the generated B-mode image data to the display image generation unit 33, and outputs the generated B-mode image data to the buffer 34. In a case where a freeze instruction signal of an image is input via the operation apparatus 4, the signal processing unit 32 extracts B-mode image data from the buffer 34 and outputs the extracted B-mode image to the display image generation unit 33, as a frozen image.

The display image generation unit 33 performs predetermined processing, such as data decimation and gradation processing corresponding to the data step size determined in accordance with the image display range on the display device 5, on the B-mode image data generated by the signal processing unit 32 and thereafter outputs the processed signal as display-oriented display image data. Moreover, the display image generation unit 33 generates display image data using the command image generated by the command image generation unit 37 and the ultrasound image. Specifically, the display image generation unit 33 generates display image data obtained by superposing the command image onto the ultrasound image, or by arranging the command image adjacent to the ultrasound image.

The buffer 34 is formed with a ring buffer, for example, and stores, along the timeline, a fixed amount (a predetermined number of frames) of B-mode images generated by the signal processing unit 32. When the capacity is insufficient (when the predetermined number of frames of B-mode image data are stored), a predetermined number of frames of the latest B-mode images are stored along the timeline by overwriting the oldest B-mode image data with the latest B-mode image data.

The executable command selection unit 35 selects a command that is executable, among a plurality of commands to be executed by the ultrasound observation apparatus 3, as the executable command, in accordance with the detection information input from the operation apparatus 4. The executable command selection unit 35 extracts, for example, a command from a plurality of commands stored in the storage unit 38, in accordance with the detection information input from the operation apparatus 4. The executable command selection unit 35 outputs information related to the selected executable command, to the control unit 39.

The execution command selection unit 36 selects a command to execute, from the commands selected by the executable command selection unit 35, in accordance with the detection information input from the operation apparatus 4. The execution command selection unit 36 outputs information related to the selected command, to the control unit 39.

The command image generation unit 37 generates a command image to be displayed on the display device 5 in order to select the command selected by the executable command selection unit 35, and an image (including information regarding coordinates) according the shape of a practitioner's finger based on the detection information input from the operation apparatus 4. The command image generation unit 37 outputs the generated command image to the display image generation unit 33.

The storage unit 38 stores various programs for operating the ultrasound diagnosis system 1, data including various parameters needed for operation of the ultrasound diagnosis system 1, or the like. The storage unit 38 includes a command information storage unit 38a.

The command information storage unit 38a stores a plurality of commands executed by the ultrasound observation apparatus 3 in association with the detection information (shape and arrangement of the practitioner's finger) input from the operation apparatus 4. The command information storage unit 38*a* stores a table that associates one or more commands with the detection information.

The storage unit 38 also stores various programs including an operation program for executing a method for operating the ultrasound diagnosis system 1. The operation programs can be recorded in a computer-readable recording medium such as a hard disk, flash memory, CD-ROM, DVD-ROM, flexible disk, or the like, and can be distributed broadly. It is also possible to obtain the above-described various programs by downloading them via a communication network. Herein, the communication network refers to one implemented by, for example, a known public network, a local area network (LAN), a wide area network (WAN), regardless of wired or wireless.

The above-configured storage unit 38 is implemented using a read only memory (ROM) in which various programs are pre-installed, a random access memory (RAM) that stores calculation parameters and data for each of processing, or the like.

The control unit 39 includes a central processing unit (CPU) having control functions, and various calculation circuits. The control unit 39 reads, from the storage unit 38, information stored in the storage unit 38, and executes various types of calculation processing related to the method for operating the ultrasound diagnosis system 1, thereby integrally controlling the ultrasound diagnosis system 1.

The operation apparatus 4 includes a display unit 41, a touch panel 42 (input receiving unit), a detection sensor unit 43, a shape detection unit 44, a position detection unit 45, a storage unit 46, and a control unit 47.

The display unit 41 includes a display panel formed with liquid crystal, organic electro luminescence (EL), or the like. The display unit 41 displays, for example, an ultrasound image that corresponds to the B-mode image data input via the control units 39 and 47, and various types of information regarding operation. The display unit 41 displays the image same as the image displayed on the display device 5, for example.

The touch panel 42 is provided on the display screen of the input the display unit 41 and receives input corresponding to the contact position of an external object. Specifically, the touch panel 42 detects a position touched (contacted) by the practitioner in accordance with the operation icons displayed on the display unit 41 and outputs an operation signal including a position signal corresponding to the detected touch position, onto the control unit 47. The display unit 41 displays the ultrasound image and various types of information, whereby the touch panel 42 functions as a graphical user interface (GUI). The touch panel includes a resistive film type, a capacitive type, an optical type, and any of these touch panels is applicable.

The detection sensor unit 43 is implemented using an infrared sensor, for example. Specifically, the detection sensor unit 43 projects infrared rays onto a region including a surface on the touch panel 42 and receives the infrared rays reflected from a practitioner's hand, or the like. The detection sensor unit 43 outputs the information (detection signal) related to the detected infrared rays to the shape detection unit 44 and the position detection unit 45.

The shape detection unit 44 detects the shape on the basis of the detection signal input from the detection sensor unit 43. Specifically, the shape detection unit 44 performs pattern matching with the signal patterns stored in the storage unit 46 on the basis of the signal pattern of the detection signal, specifically, the signal pattern of the signal that is received by reflection, thereby detecting the shape and arrangement of the practitioner's finger.

The position detection unit 45 detects a position of a detection target on the basis of the detection signal input from the detection sensor unit 43. Specifically, the position detection unit 45 calculates the distance between the detection sensor unit 43 and a practitioner's finger on the basis of the detection signal, thereby detecting the spatial position of the practitioner's hand (hereinafter, referred to as a "position of practitioner's hand") with respect to the surface (contact surface) of the touch panel (display unit 41). The spatial position of the practitioner's hand is a position (coordinates) relative to a contact surface of the touch panel 42. This relative position is associated with the image (display section) displayed on the display unit 41.

The detection sensor unit 43, the shape detection unit 44, and the position detection unit 45 constitute a detection unit. Detection processing performed by the detection unit would be performed using a conventional technique disclosed in JP 4899806 B1, for example, in the case of performing the above-described processing using infrared rays. Detection of arrangement and shape of the finger, detection of the position of the practitioner's hand with respect to the touch panel 42 (display unit 41) are not limited to these but may be detected by known techniques. For example, it is allowable to configure to image a region on the touch panel 42, and then, detect the arrangement and shape of the finger and the spatial position of the practitioner's hand with respect to the touch panel 42 (display unit 41) on the basis of the obtained image.

The storage unit 46 stores various programs for operating the operation apparatus 4, data including various parameters needed for operation of the operation apparatus 4, or the like. The various programs can be recorded in a computer-readable recording medium such as a hard disk, flash memory, CD-ROM, DVD-ROM, flexible disk, or the like, and can be distributed broadly. It is also possible to obtain the above-described various programs by downloading them via a communication network. Herein, the communication network refers to one implemented by, for example, a known public network, a local area network (LAN), a wide area network (WAN), regardless of wired or wireless.

The storage unit 46 includes a shape information storage unit 46*a*. The shape information storage unit 46*a* stores a shape pattern of a finger of the practitioner who operates the operation apparatus 4. Specifically, the shape information storage unit 46*a* stores a signal pattern obtained by the detection signal, in association with the shape pattern of the finger.

The above-configured storage unit 46 is implemented using a read only memory (ROM) in which various programs are pre-installed, a random access memory (RAM) that stores calculation parameters and data for each of processing, or the like.

The control unit 47 controls the overall operation apparatus 4. The control unit 47 includes a central processing unit (CPU) having calculation and control functions, various calculation circuits, or the like.

Figure 2:
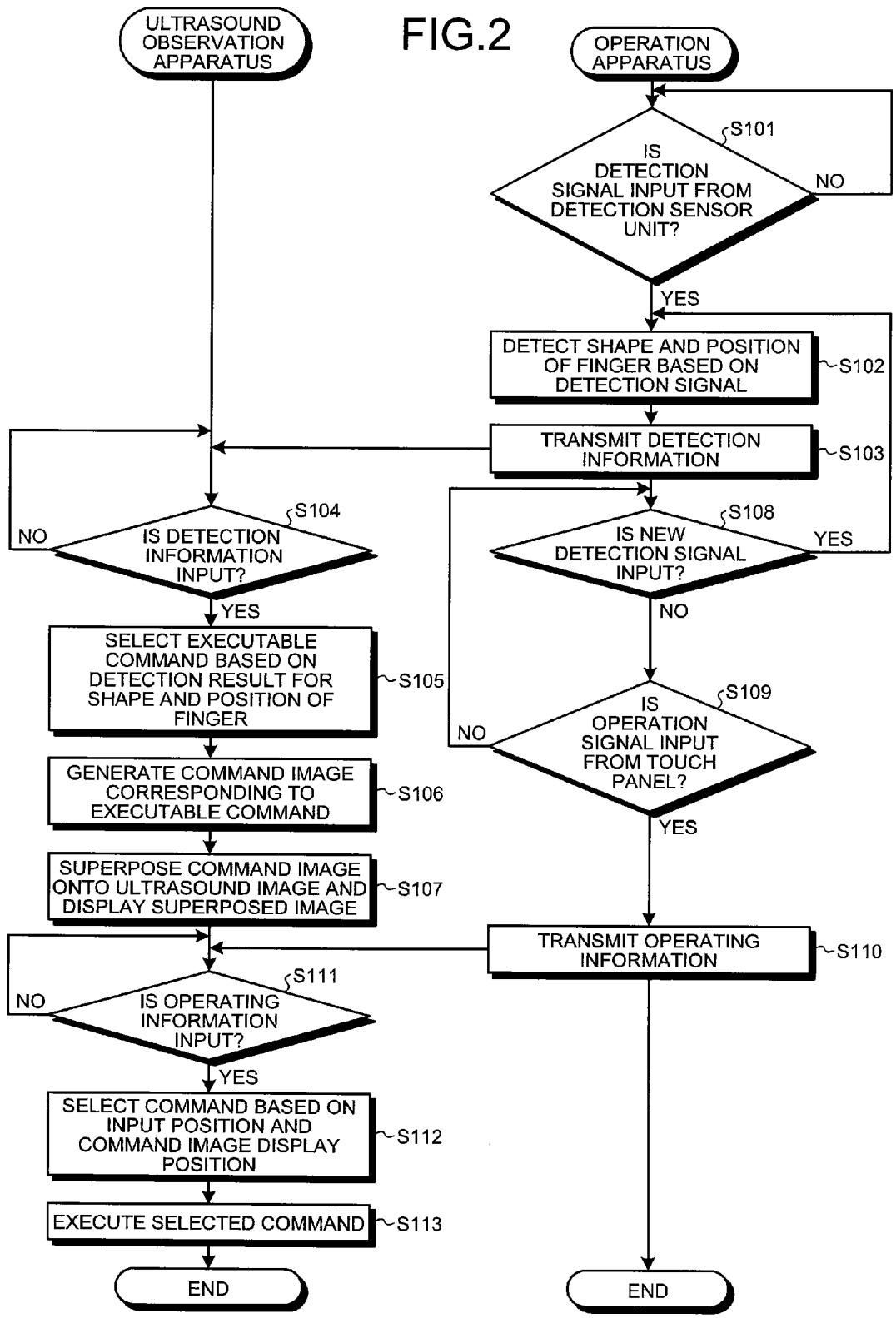
FIG. 2 is a flowchart illustrating command execution processing performed by the ultrasound diagnosis system according to the first embodiment of the present invention.

Next, command execution processing performed by the above-configured ultrasound diagnosis system 1 will be described with reference to the drawings. FIG. 2 is a flowchart illustrating command execution processing performed by the ultrasound diagnosis system according to the first embodiment. The following description of the command execution processing will be given on the assumption that the B-mode images sequentially generated on the display image generation unit 33 are at least displayed in a live image on the display device 5.

First, the control unit 47 of the operation apparatus 4 judges the presence or absence of input of a detection signal from the detection sensor unit 43 (step S101). In a case where the detection signal input is present (step S101: Yes), the control unit 47 proceeds to step S102. In contrast, in a case where the detection signal input is absent (step S101: No), the control unit 47 returns to step S101 and repeats confirmation of input of the detection signal.

In step S102, the shape detection unit 44 and the position detection unit 45 detect arrangement and the shape of the finger and the position of the practitioner's hand with respect to the touch panel 42 (display unit 41) (detection step) on the basis of the detection signal. The shape detection unit 44 and the position detection unit 45 output detection information including detected arrangement and the shape of the finger and the position (coordinates) of the practitioner's hand with respect to the touch panel 42 (display unit 41) onto the control unit 47. The control unit 47 outputs obtained detection information to the control unit 39 of the ultrasound observation apparatus 3 (step S103). Note that the practitioner's hand is not in contact with the touch panel 42 at this point.

On the ultrasound observation apparatus 3, the control unit 39 judges the presence or absence of input of detection information from the operation apparatus 4 (step S104). In a case where detection information judges that input of detection information is absent (step S104: No), the control unit 39 repeats confirmation of input of detection information. In contrast, in a case where the control unit 39 judges that the input of detection information is present (step S104: Yes), the control unit 39 proceeds to step S105.

In step S105, the executable command selection unit 35 selects a command that is executable, among a plurality of commands executed by the ultrasound observation apparatus 3, as the executable command, in accordance with the detection information input from the operation apparatus 4 or an operation mode of the ultrasound observation apparatus 3 (command selection step). The operation mode herein represents an operation mode related to display (observation) of the B-mode image, for example, live display, freeze display, and a scan mode related to ultrasound scanning. In the case of the ultrasound endoscope system including an ultrasound endoscope described below, the operation mode includes a display mode of an in-vivo image of the subject. The following will be described on the assumption that the operation mode is set to the operation mode related to the live display.

In the first embodiment, the position (coordinates) of the practitioner's hand and the coordinates attached to the display screen of the display unit 41 are associated with each other. Executable commands are different in a case where the practitioner's hand is arranged within a B-mode mode image display region on the display unit 41, from the case where the practitioner's hand is arranged outside the B-mode image display region. For example, in a case where the practitioner's hand is arranged outside the B-mode image display region, it is possible to select commands related to observation modes such as a pulsed Doppler (PW) mode, a flow (FLOW) mode, a contrast harmonic (CH) mode, and an elastography (ELST) mode, as the executable commands.

The pulsed Doppler mode is a mode of analyzing the Doppler shift in a set region (sample volume) and obtaining temporal change information of the blood flow (pulsed Doppler waveform) in the sample volume. The flow mode is a mode of obtaining blood flow information, that is, information regarding the blood flow, by analyzing the Doppler shift in a set region (hereinafter, also referred to as a flow region-of-interest (ROI)) and superposing color information corresponding to the direction of the blood flow, onto the B-mode image. The contrast harmonic mode is a mode of imaging a harmonic component from the ultrasound contrast agent. The elastography mode is a mode of obtaining information regarding the hardness of the observation target in a set region (hereinafter, also referred to as an elastography region-of-interest (ROI)) and superposing color information corresponding to the hardness, onto the B-mode image.

In another case where the practitioner's hand is arranged within the B-mode image display region, executable commands can be selected from any of commands related to the processing modes for the B-mode image, such as a comment input mode, cursor input mode, enlargement and reduction of the B-mode image, addition of the B-mode image, scrolling, rotation, and distance measurement.

After command selection is performed by the executable command selection unit 35, the command image generation unit 37 generates a command image for displaying the command selected by the executable command selection unit 35 (step S106: command image generation step). Specifically, with reference to the command information storage unit 38a, the command image generation unit 37 obtains a display-oriented command image corresponding to the command selected by the executable command selection unit 35 and outputs the obtained command image to the display image generation unit 33, as the display-oriented command image data.

Thereafter, the display image generation unit 33 performs processing of superposing the command image input from the command image generation unit 37 onto the B-mode image data (ultrasound image) together with the image of the shape of the practitioner's finger (finger shape image) detected by the shape detection unit 44, performing predetermined signal processing to generate display image data, and displaying the display image data onto the display device 5 (step S107: display image generation step).

Figure 3:
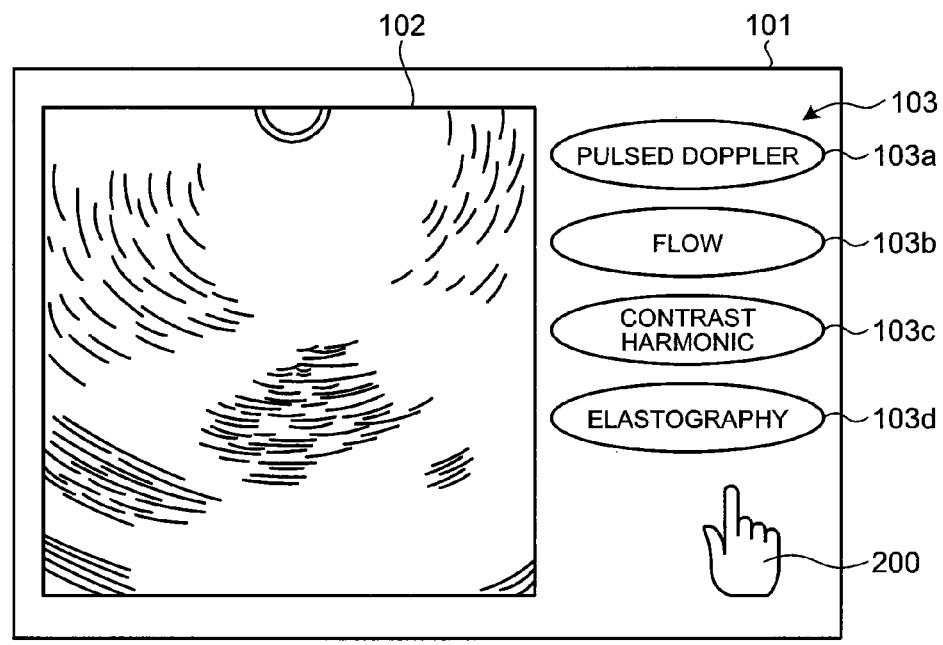
FIG. 3 is a diagram illustrating a display image in the command execution processing according to the first embodiment of the present invention.

FIG. 3 is a diagram illustrating a display image in the command execution processing according to the first embodiment, displayed on a display unit 101 of the display device 5 when the practitioner's finger is placed at a position corresponding to the position outside the B-mode image display region on the touch panel 42 (display unit 41). The display unit 101 includes an ultrasound image display section 102 and an information display section 103. The ultrasound image display section 102 displays the B-mode image. The information display section 103 is a region different from the ultrasound image display section 102 and can display various types of information such as a command image. The ultrasound image display section 102 displays an image of the region-of-interest (ROI), that is, a predetermined region that has been set, among operation ranges of the ultrasound transducer 21.

For example, in a case where the practitioner's finger is located at a position on the touch panel 42 (display unit 41) with the index finger raised, at a position corresponding to the position outside the region of the ultrasound image display section 102, the image of the practitioner's finger (pointer 200) is arranged in accordance with the position on the touch panel 42, and command images 103a to 103d corresponding to the commands selected by the executable command selection unit 35 are displayed on the information display section 103, as illustrated in FIG. 3. The command image 103a is a command image representing the pulsed Doppler mode. The command image 103b is a command image representing the flow mode. The command image 103c is a command image representing the contrast harmonic mode. The command image 103d is a command image representing the elastography mode.

Figure 4:
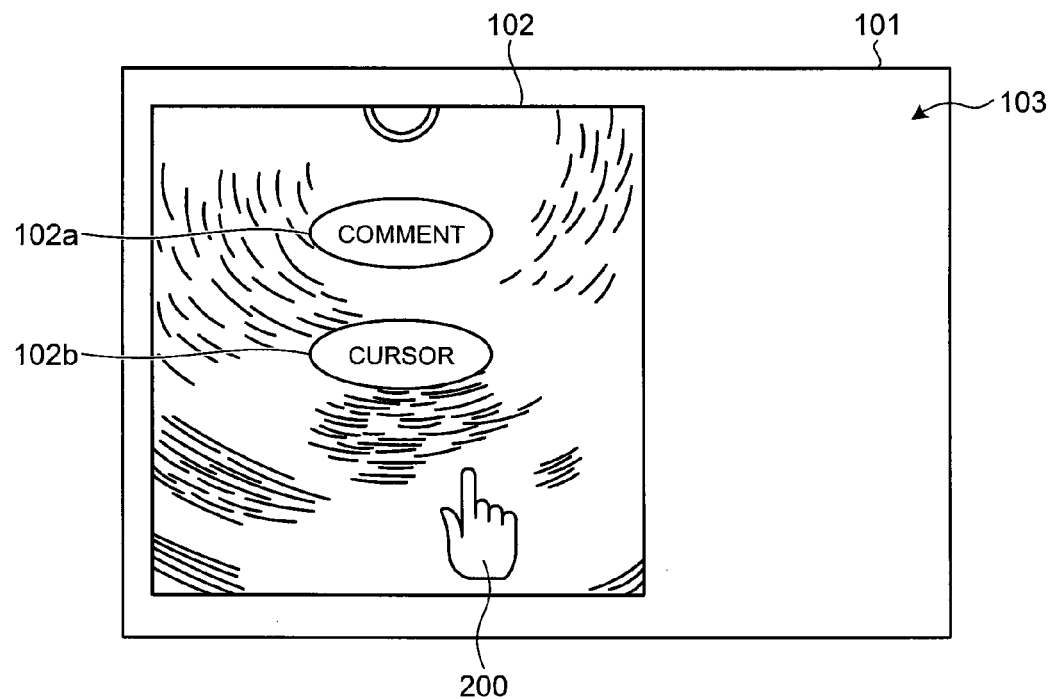
FIG. 4 is a diagram illustrating a display image in the command execution processing according to the first embodiment of the present invention.

FIG. 4 is a diagram illustrating a display image in the command execution processing according to the first embodiment, and this diagram is displayed on the display unit 101 of the display device 5 in a case where the practitioner's finger is arranged at a position corresponding to the position within the B-mode image display region on the touch panel 42 (display unit 41). For example, in a case where the practitioner's finger is located at a position on the touch panel 42 (display unit 41) with the index finger raised, at a position corresponding to the position within the region of the ultrasound image display section 102, the image of the practitioner's finger (pointer 200) is arranged in accordance with the position on the touch panel 42, and command images 102a and 102b corresponding to the commands selected by the executable command selection unit 35 are displayed on the ultrasound image display section 102, as illustrated in FIG. 4. The command image 102a is the command image representing a comment input mode. The command image 102b is a command image representing the cursor input mode.

Figure 5:
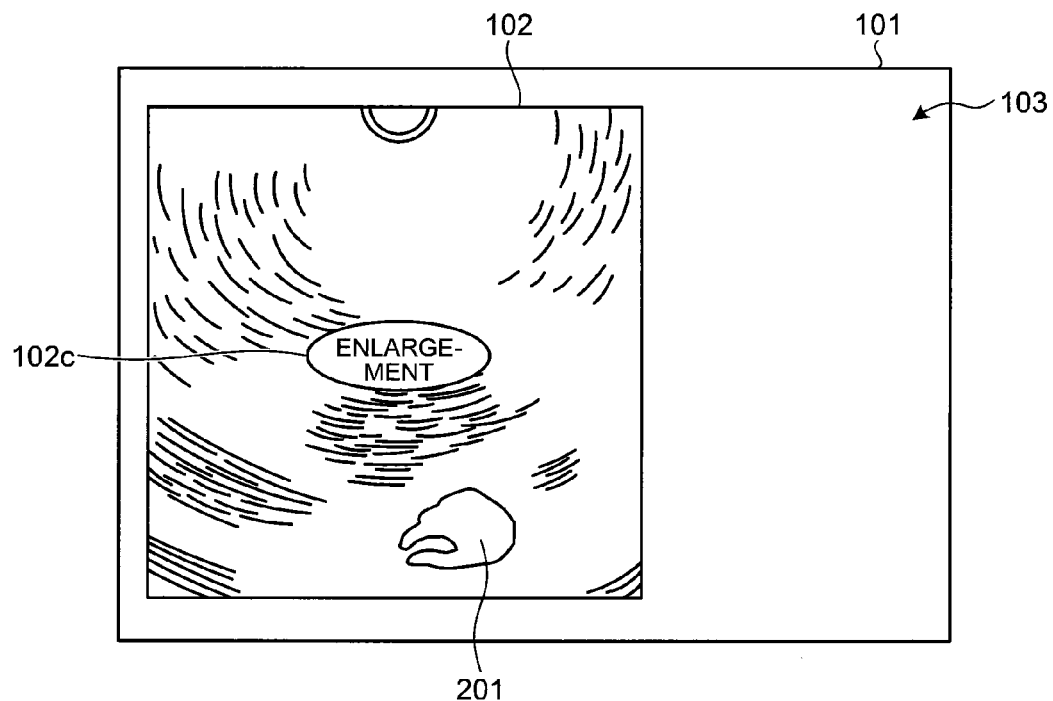
FIG. 5 is a diagram illustrating a display image in the command execution processing according to the first embodiment of the present invention.

FIG. 5 is a diagram illustrating a display image in the command execution processing according to the first embodiment, displayed on the display unit 101 of the display device 5 in a case where the practitioner's finger is arranged at a position corresponding to the position within the B-mode image display region on the touch panel (display unit 41). For example, in a case where the practitioner's finger is located at a position on the touch panel 42 (display unit 41) with the thumb and the index finger being close to each other, at a position corresponding to the position on the ultrasound image display section 102, the image of the practitioner's finger (pointer 201) is arranged in accordance with the position on the touch panel 42, and a command image 102c corresponding to the command selected by the executable command selection unit 35 is displayed on the ultrasound image display section 102, as illustrated in FIG. 5. The command image 102c is a command image representing an enlargement mode, or a display range mode for changing the display mode, for the B-mode image.

Figure 6:
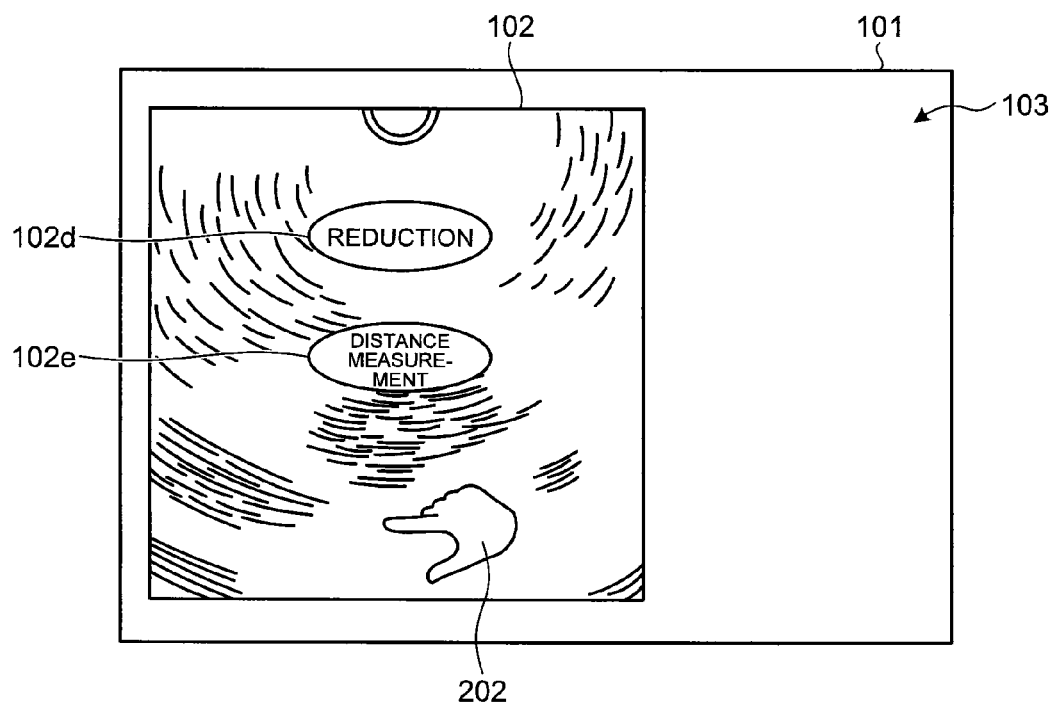
FIG. 6 is a diagram illustrating a display image in the command execution processing according to the first embodiment of the present invention.

FIG. 6 is a diagram illustrating a display image in the command execution processing according to the first embodiment, displayed on the display unit 101 of the display device 5 in a case where the practitioner's finger is arranged at a position corresponding to the position within the B-mode image display region on the touch panel 42 (display unit 41). For example, in a case where the practitioner's finger is located at a position on the touch panel 42 (display unit 41) with the thumb and the index finger being separated from each other, at a position corresponding to the position on the ultrasound image display section 102, the image of the practitioner's finger (pointer 202) is arranged in accordance with the position on the touch panel 42, and command images 102d and 102e corresponding to the commands selected by the executable command selection unit 35 are displayed on the ultrasound image display section 102, as illustrated in FIG. 6. The command image 102d is a command image representing a reduction mode of the B-mode image. The command image 102e is a command image representing a distance measurement mode for measuring the distance between designated two points, or a display range mode.

Note that while the configuration of the pointers 200 to 202 is preferable in that it is possible, by indicating the shape of the finger, to confirm whether the shape matches the shape intended by the practitioner, the pointers are not limited to this but may have other shapes, such as arrows. Furthermore, as a command image display mode in a case where the pointers 201 and 202 exist on the ultrasound image display section 102, it is configured such that the command image is arranged at a position separated from the image of the ultrasound transducer 21 on the B-mode image (semicircle above the ultrasound image display section 102 in FIGS. 5 and 6) by a fixed distance or more. With this configuration, it is possible to prevent an error in selecting a command (command image) further reliably.

Back to the flowchart in FIG. 2, when a new detection signal from the detection sensor unit 43 is present (step S108: Yes), the control unit 47 returns to step S102 and repeats the above-described display processing. In contrast, when the new detection signal from the detection sensor unit 43 is absent (step S108: No), the control unit 47 proceeds to step S109.

In step S109, the control unit 47 judges whether an operation signal has been input from the touch panel 42. When the control unit 47 judges that the operation signal has not been input from the touch panel 42 (step S109: No), the control unit 47 returns to step S107 and repeats confirmation processing on the detection signal and the operation signal. In contrast, when the control unit 47 judges that the operation signal has been input from the touch panel 42 (step S109: Yes), the control unit 47 outputs operating information according to the operation signal to the control unit 39 (step S110).

On the ultrasound observation apparatus 3, the control unit 39 judges the presence or absence of input of operating information from the operation apparatus 4 (step S111). In a case where the control unit 39 judges that operating information input is absent (step S111: No), the control unit 39 repeats confirmation of input of operating information. In contrast, in a case where the control unit 39 judges that the input of detection information is present (step S111: Yes), the control unit 39 proceeds to step S112.

In step S112, the execution command selection unit 36 determines the selected command image on the basis of input position coordinates on the touch panel 42 and the command image display position coordinates and selects a command corresponding to the selected command image, as a command to execute. The execution command selection unit 36 outputs information related to the selected command, to the control unit 39. The control unit 39 performs control of execution of the selected command (step S113).

For example, when the command image 103b is selected in a state indicated in FIG. 3, the control unit 39 switches the observation mode to the flow mode. In some cases command selection processing is performed after the mode is switched to the flow mode. In this case, further command execution processing would be possible by executing the above-described steps S102 to S113.

Figure 7:
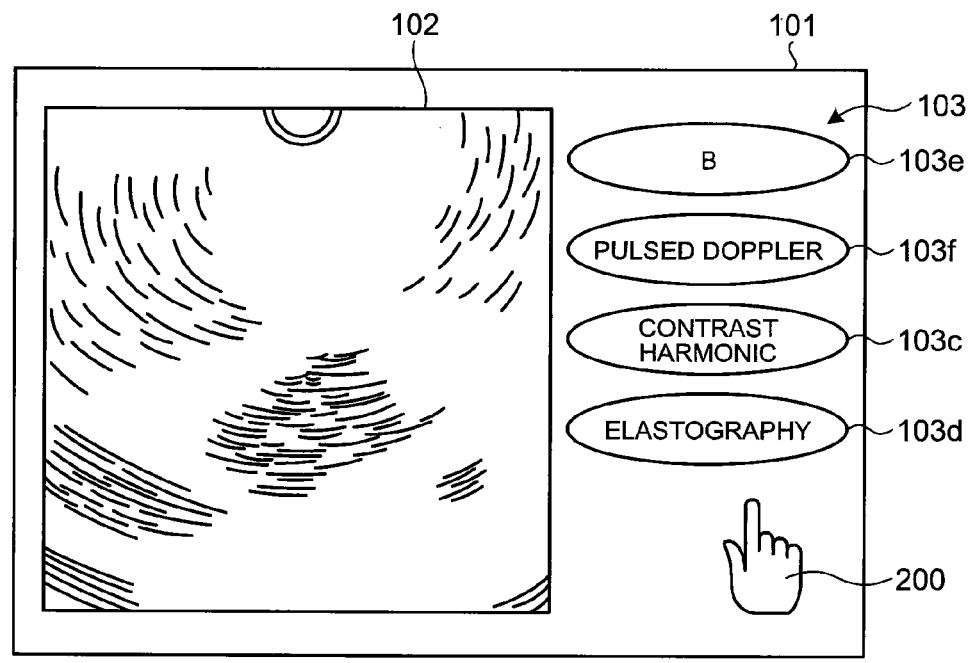
FIG. 7 is a diagram illustrating a display image in the command execution processing according to the first embodiment of the present invention.

FIG. 7 is a diagram illustrating a display image in the command execution processing according to the first embodiment, displayed on the display unit 101 of the display device 5 in a case where the practitioner's finger is arranged at a position corresponding to the position outside the B-mode image display region on the touch panel 42 (display unit 41) in a state where the mode is set to the flow mode.

For example, in a case where the practitioner's finger is located at a position on the touch panel 42 (display unit 41) with the index finger raised, at a position corresponding to the position outside the region of the ultrasound image display section 102, the image of the practitioner's finger (pointer 200) is arranged in accordance with the position on the touch panel 42, and command images 103c to 103f corresponding to the commands selected by the executable command selection unit 35 are displayed on the information display section 103, as illustrated in FIG. 7. The command image 103e is the command image representing a B-mode image display mode. The command image 103f is a command image representing the pulsed Doppler mode. When a command is selected by the operation on the touch panel 42 described above, the mode is switched, by the control unit 39, to the observation mode corresponding to the selected command.

Figure 8:
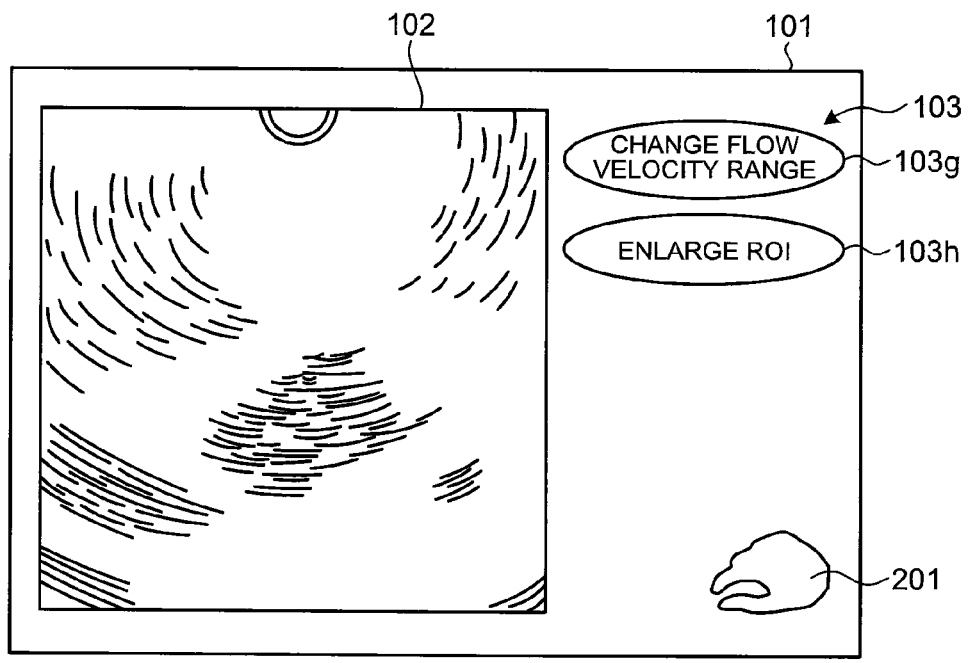
FIG. 8 is a diagram illustrating a display image in the command execution processing according to the first embodiment of the present invention.

FIG. 8 is a diagram illustrating a display image in the command execution processing according to the first embodiment, displayed on the display unit 101 of the display device 5 in a case where the practitioner's finger is located at a position corresponding to the position outside the region of the ultrasound image display section 102 on the touch panel 42 (display unit 41). For example, in a case where the practitioner's finger is located at a position on the touch panel 42 (display unit 41) with the thumb and the index finger being close to each other, at a position corresponding to the position within the region on the ultrasound image display section 102, the image of the practitioner's finger (pointer 201) is arranged in accordance with the position on the touch panel 42, and command images 103g and 103h corresponding to the command selected by the executable command selection unit 35 are displayed on the ultrasound image display section 102, as illustrated in FIG. 8. The command image 103g is a command image representing a flow velocity range change mode for changing the flow velocity range of the blood flow. The command image 103h is a command image representing a region-of-interest enlargement mode for enlarging the region-of-interest.

Figure 9:
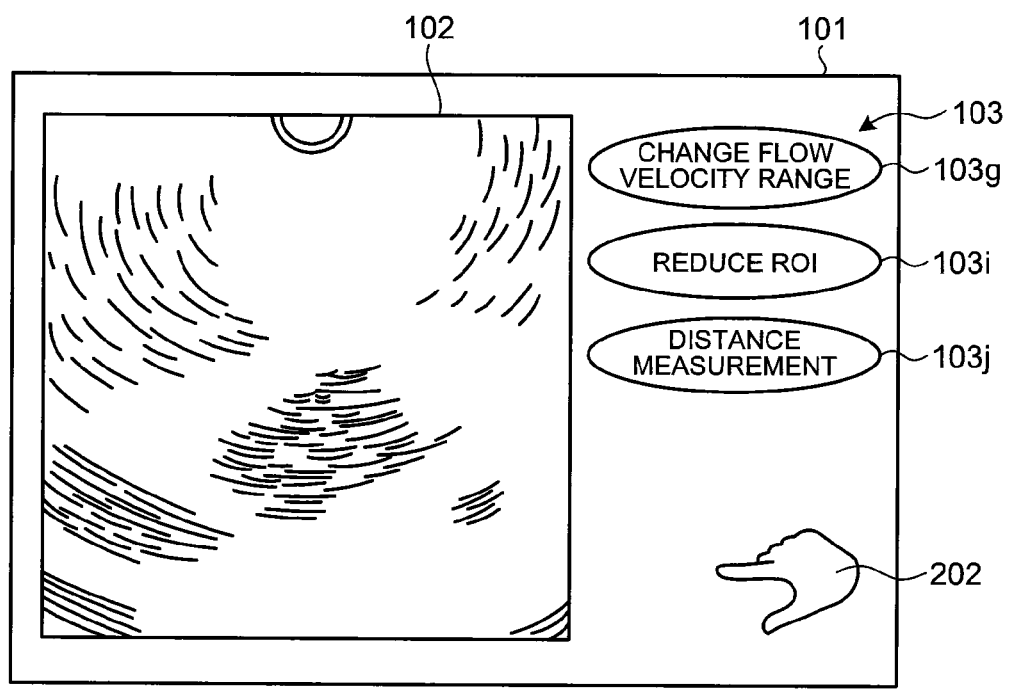
FIG. 9 is a diagram illustrating a display image in the command execution processing according to the first embodiment of the present invention.

FIG. 9 is a diagram illustrating a display image in the command execution processing according to the first embodiment, displayed on the display unit 101 of the display device 5 in a case where the practitioner's finger is located at a position corresponding to the position outside the region of the ultrasound image display section 102 on the touch panel 42 (display unit 41). For example, in a case where the practitioner's finger is located at a position on the touch panel 42 (display unit 41) with the thumb and the index finger being separated from each other, at a position corresponding to the position within the region on the ultrasound image display section 102, the image of the practitioner's finger (pointer 202) is arranged in accordance with the position on the touch panel 42, and command images 103g, 103i, and 103j corresponding to the commands selected by the executable command selection unit 35 are displayed on the ultrasound image display section 102, as illustrated in FIG. 9. The command image 103i is a command image representing a region-of-interest reduction mode for reducing the region-of-interest. The command image 103j is a command image representing the distance measurement mode for measuring the distance between designated two points in the flow mode.

Also in FIGS. 8 and 9, when a command is selected by the operation on the touch panel 42 described above, the mode is switched, by the control unit 39, to the mode corresponding to the selected command. After the mode is switched to each of modes, processing according to the mode is further performed. For example, the comment input mode is configured such that an image for instructing a comment input position is displayed on the ultrasound image display section 102. The practitioner performs selection and instruction via the touch panel 42, thereby designating a comment input position, and thereafter, enabling input of a comment with a keyboard or by voice. The cursor input mode is configured such that an image for instructing a cursor input position is displayed on the ultrasound image display section 102. The practitioner performs selection and instruction via the touch panel 42, thereby enabling designation of the cursor input position.

The B-mode image enlargement mode is configured such that the mode is switched to an input reception mode for enlarging the image. The practitioner performs instruction, for example, for pinching out, via the touch panel 42, thereby enabling enlargement of the image. In contrast, the B-mode image reduction mode is configured such that the mode is switched to an input reception mode for reducing the image, and when the practitioner performs instruction, for example, for pinching in, via the touch panel 42, thereby enabling reduction of the image.

In the distance measurement mode, the mode is switched to an input reception mode that receives an instruction of a starting point and an ending point for measurement, and with an instruction of two points on the B-mode image by the practitioner, for example, using the thumb and the index finger via the touch panel 42, it is possible to measure the distance of a line having the instructed two points determined as the starting point and the ending point.

A flow velocity display range change mode is configured such that an image for changing the flow velocity range is displayed on the information display section 103. The practitioner performs selection and instruction via the touch panel 42, thereby enabling changing the flow velocity range.

The region-of-interest enlargement mode is configured such that the mode is switched to an input reception mode for enlarging the region-of-interest (ROI) as a setting region of the flow mode. The practitioner performs instruction, for example, for pinching out, via the touch panel 42, thereby enabling enlargement of the ROI. In contrast, the region-of-interest reduction mode is configured such that the mode is switched to an input reception mode for reducing the region-of-interest (ROI) as a setting range of the flow mode. The practitioner performs instruction, for example, for pinching in, via the touch panel 42, thereby enabling reduction of the ROI.

According to the above-described first embodiment, it is configured such that executable command is selected and displayed on the display device 5 on the basis of the detected arrangement and shape of the finger and on the basis of the practitioner's hand position with respect to the touch panel 42 (display unit 41), and that the command to execute is selected by touch operation on the touch panel 42. With this configuration, it is possible to perform input operation with high flexibility without removing eyes from the monitor (display unit 101). Moreover, according to the first embodiment, it is possible to select and execute a command while confirming the display unit 101. Accordingly, it is possible to achieve an effect of suppressing an error in operation.

The above-described first embodiment assumes the selection of commands related to the observation modes such as the pulsed Doppler mode, the flow mode, the contrast harmonic mode, and the elastography mode. The mode is not limited to this, but may be a tissue harmonic mode, or the like.

Moreover, the above-described first embodiment assumes that the shape detection unit 44 and the position detection unit 45 are provided on the operation apparatus 4. Alternatively, the shape detection unit 44 and the position detection unit 45 may be provided on the ultrasound observation apparatus 3 or the display device 5. In this case, the shape information storage unit 46a may also preferably be provided in the storage unit 38.

In the above-described first embodiment, the display unit 41 displays the image same as the image displayed on the display device 5. Alternatively, the display unit 41 may display a different image or an image for guiding operation, or may display no image.

Modification Example of First Embodiment

Figure 10:
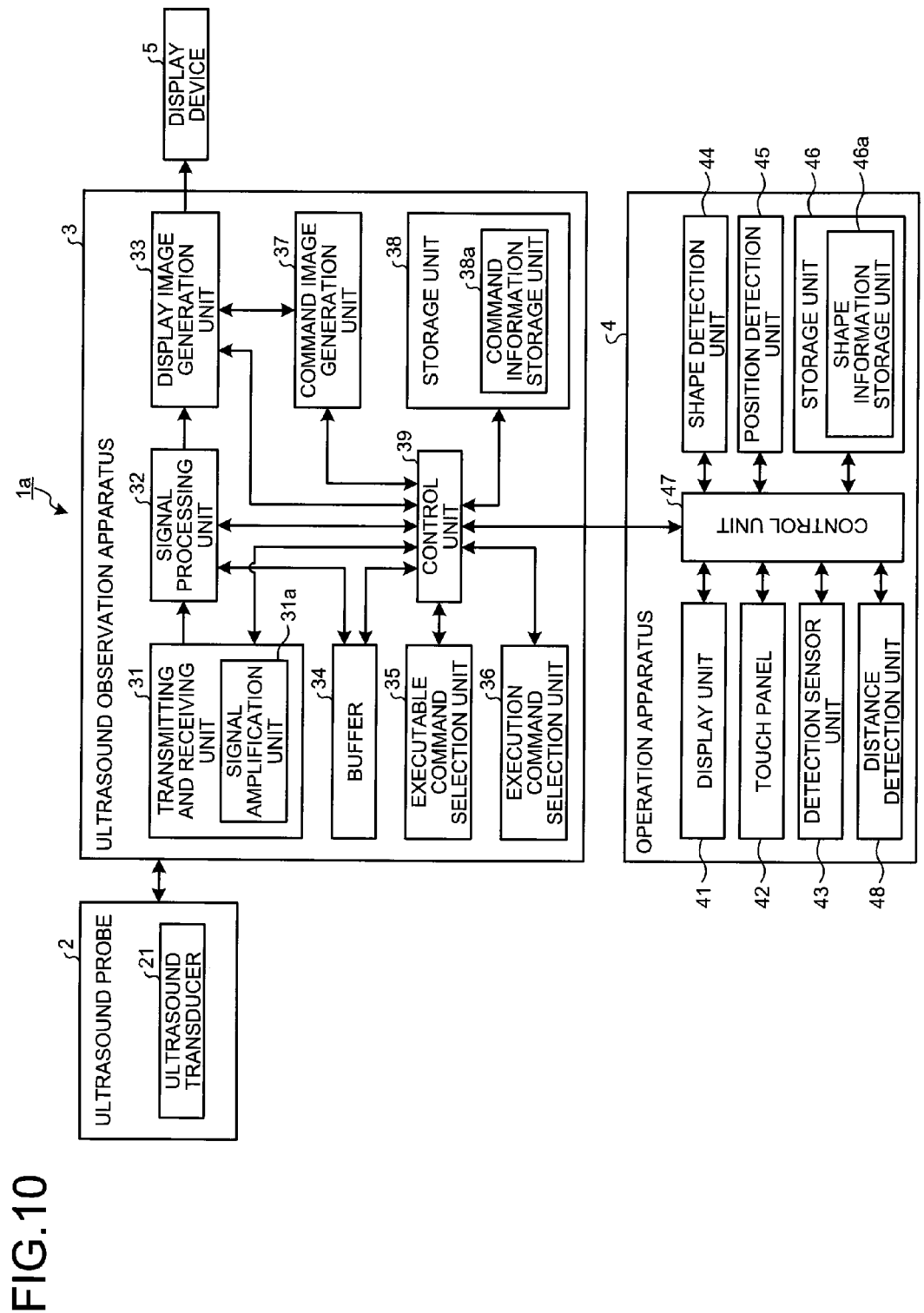
FIG. 10 is a block diagram illustrating a configuration of an ultrasound diagnosis system according to a modification example of the first embodiment of the present invention.

Next, a modification example of the first embodiment of the present invention will be described with reference to the drawings. FIG. 10 is a block diagram illustrating a configuration of an ultrasound diagnosis system according to a modification example according to the first embodiment. The above-described first embodiment assumes that an executable command is selected and displayed on the basis of the detected arrangement and shape of the finger, and on practitioner's hand position with respect to the touch panel 42 (display unit 41). Furthermore, in the present modification example, the command image is highlighted in accordance with the distance between the detected finger and the touch panel 42.

An ultrasound diagnosis system 1a illustrated in FIG. 10 has the above-described configuration of the ultrasound diagnosis system 1, and in addition to this, the operation apparatus 4 includes a distance detection unit 48. The distance detection unit 48 detects a distance being a minimum distance between the practitioner's fingertip and the surface of the touch panel 42 on the basis of the detection signal of the detection sensor unit 43. Moreover, in the present modification example, the storage unit 38 stores a threshold related to the minimum distance between the practitioner's finger and the surface of the touch panel 42.

Figure 11:
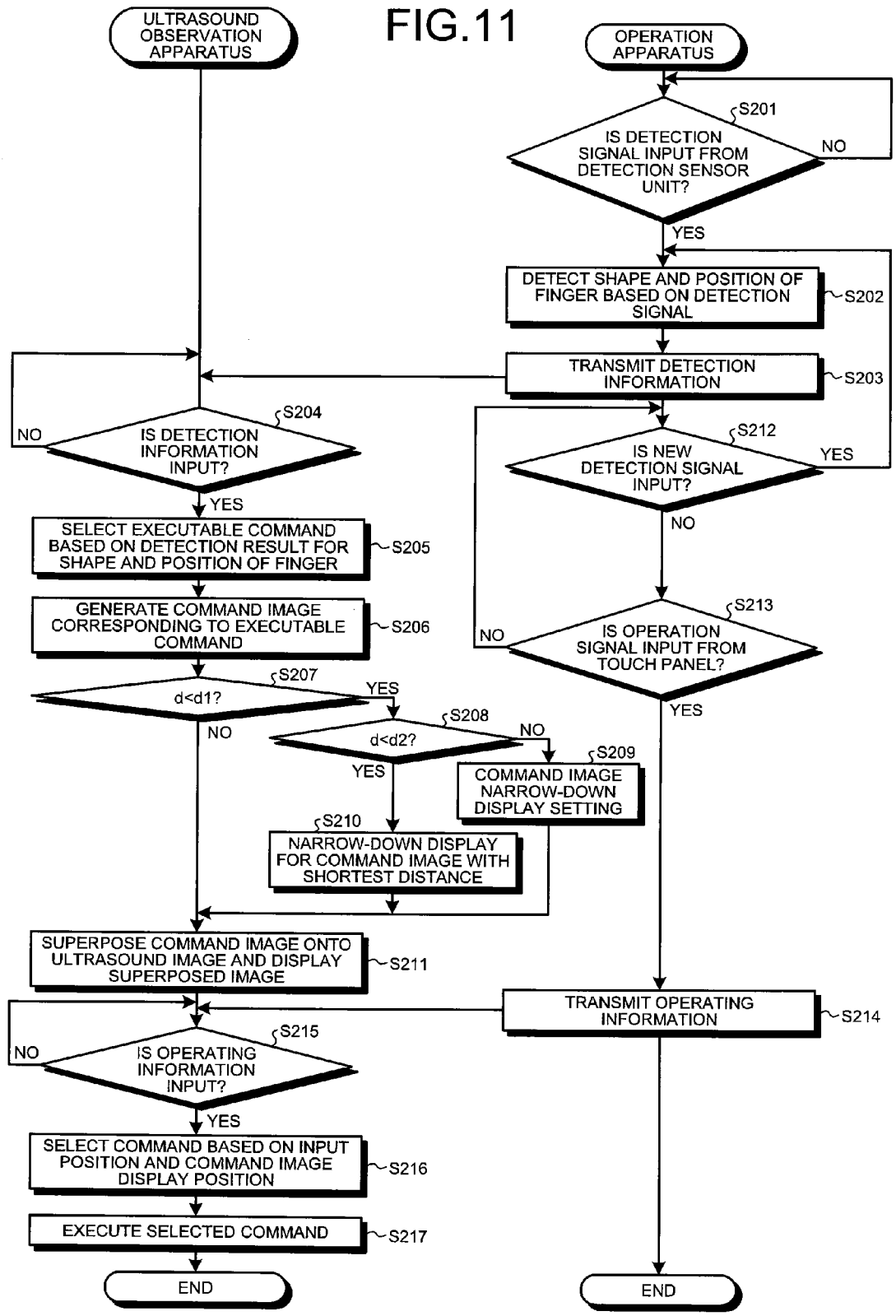
FIG. 11 is a flowchart illustrating command execution processing performed by the ultrasound diagnosis system according to the modification example of the first embodiment of the present invention.

Next, command execution processing performed by the above-configured ultrasound diagnosis system 1a will be described with reference to the drawings. FIG. 11 is a flowchart illustrating command execution processing performed by the ultrasound diagnosis system according to the modification example of the first embodiment. First, similarly to the above-described first embodiment, the control unit 47 of the operation apparatus 4 judges the presence or absence of input of a detection signal from the detection sensor unit 43 (step S201). In a case where the detection signal input is present (step S201: Yes), the control unit 47 proceeds to step S202. In contrast, in a case where the detection signal input is absent (step S201: No), the control unit 47 returns to step S201 and repeats confirmation of input of the detection signal.

In step S202, the shape detection unit 44 and the position detection unit 45 detect arrangement and shape of the finger and the position of the practitioner's hand with respect to the touch panel 42 (display unit 41) on the basis of the detection signal. The shape detection unit 44 and the position detection unit 45 output detection information including detected arrangement and shape of the finger and the position of the practitioner's hand with respect to the touch panel 42 (display unit 41), onto the control unit 39 via the control unit 47 (step S203). Note that the practitioner's hand is not in contact with the touch panel 42 at this point.

On the ultrasound observation apparatus 3, the control unit 39 judges the presence or absence of input of detection information from the operation apparatus 4 (step S204). In a case where the control unit 39 judges that the detection information input is absent (step S204: No), the control unit 39 repeats confirmation of input of detection information. In contrast, in a case where the control unit 39 judges that the input of detection information is present (step S204: Yes), the control unit 39 proceeds to step S205.

In step S205, the executable command selection unit 35 selects a command that is executable, among a plurality of commands to be executed by the ultrasound observation apparatus 3, as the executable command, in accordance with the detection information input from the operation apparatus 4 or an operation mode of the ultrasound observation apparatus 3.

After command selection by the executable command selection unit 35, the command image generation unit 37 generates a command image for displaying the command selected by the executable command selection unit 35 (step S206).

Figure 12:
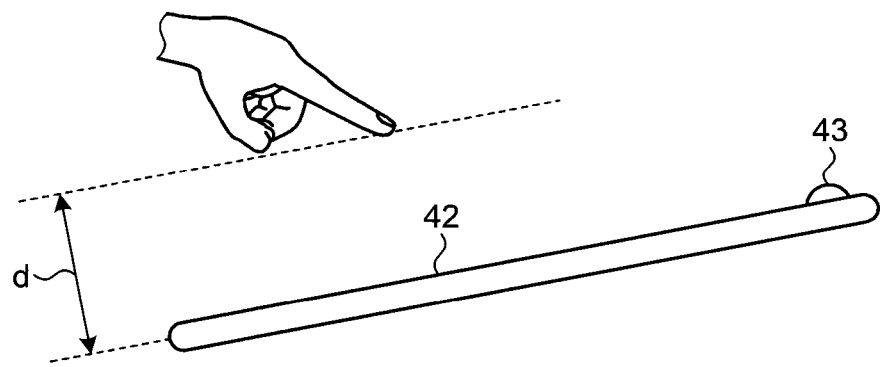
FIG. 12 is a diagram illustrating distance detection processing in the command execution processing according to the modification example of the first embodiment of the present invention.

Thereafter, the distance detection unit 48 detects a distance (minimum distance), that is, a minimum distance between the practitioner's fingertip and the surface of the touch panel 42 on the basis of the detection signal of the detection sensor unit 43. FIG. 12 is a diagram illustrating distance detection processing in the command execution processing according to the modification example of the first embodiment. The distance detection unit 48 detects a distance d, that is, a minimum distance between the practitioner's fingertip and the surface of the touch panel 42 as illustrated in FIG. 12. Distance calculation by the distance detection unit 48 is calculated using a known method such as a method using infrared rays. The distance d detected by the distance detection unit 48 is output onto the control unit 39 via the control unit 47.

The control unit 39 compares the distance d detected by the distance detection unit 48 with the threshold stored in the storage unit 38 and judges the relative positional relationship between the practitioner's fingertip and the surface of the touch panel 42 (steps S207 and S208). In step S207, the control unit 39 compares the distance d with a first threshold $d_1$, and judges whether the distance d is smaller than the first threshold $d_1$. When the control unit 39 judges that the distance d is the first threshold $d_1$ or above (step S207: No), the control unit 39 proceeds to step S209. In contrast, in a case where the control unit 39 judges that the distance d is smaller than the first threshold $d_1$ (step S207: Yes), the control unit 39 proceeds to step S207.

In step S208, the control unit 39 compares the distance d with a second threshold $d_2$ ($<d_1$), and judges whether the distance d is smaller than the second threshold $d_2$. When the control unit 39 judges that the distance d is the second threshold $d_2$ or above (step S208: No), the control unit 39 proceeds to step S209. In contrast, in a case where the control unit 39 judges that the distance d is smaller than the second threshold $d_2$ (step S208: Yes), the control unit 39 proceeds to step S210.

In step S209, the control unit 39 performs command image setting for highlighting the execution command image, such as highlighting a command image selectable by the position of the finger, among the plurality of command images. As determined in step S207, when the distance d between the practitioner's fingertip and the surface of the touch panel 42 is the second threshold $d_2$ or above and smaller than the first threshold $d_1$, the control unit 39 performs setting for selecting a command image including the coordinates positioned at a minimum distance from the finger and selecting another command image spatially adjoining the command image, and setting for narrow-down display (highlight) for the selected command images.

Also in step S210, the control unit 39 performs command image setting for highlighting the execution command image. As determined in step S208, in a case where the distance d between the practitioner's fingertip and the surface of the touch panel 42 is smaller than the second threshold $d_2$, it means the state in which the practitioner's fingertip and the surface of the touch panel 42 are in close proximity. Accordingly, the control unit 39 performs setting for selectively highlighting the command image including the coordinates positioned at a minimum distance from the finger.

The display image generation unit 33 performs processing of superposing the command image input from the command image generation unit 37 onto the B-mode image data together with the image of the shape of the practitioner's finger detected by the shape detection unit 44, generating display image data so as to highlight the command image for which highlight display setting is performed, and displaying the display image data onto the display device 5 (step S211).

Figure 13:
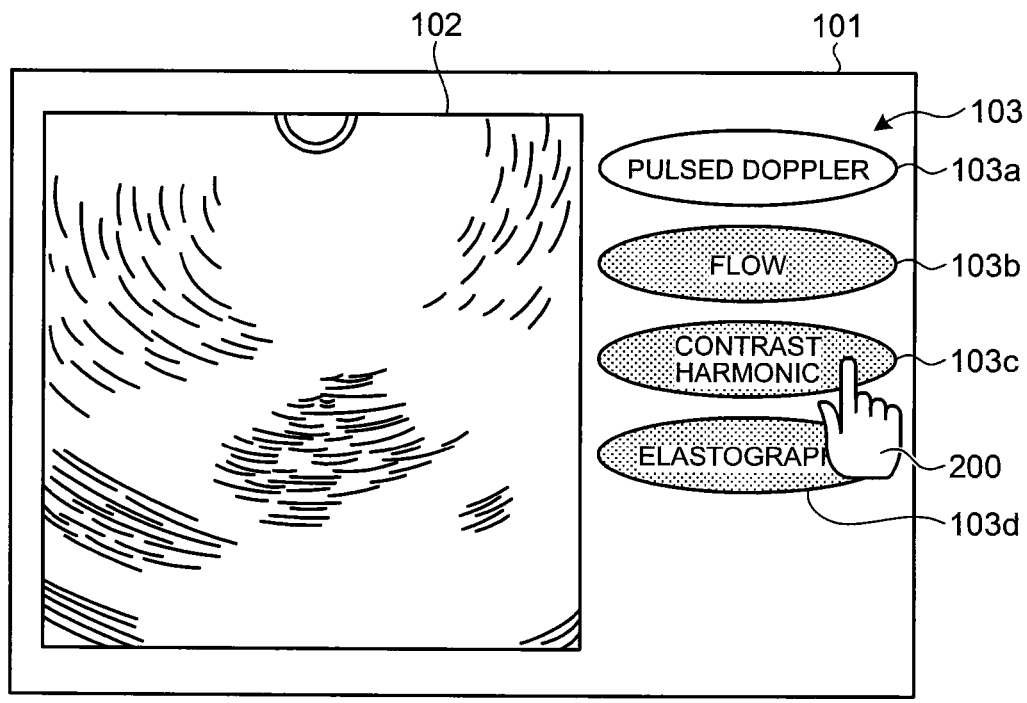
FIG. 13 is a diagram illustrating a display image in the command execution processing according to the modification example of the first embodiment of the present invention.

FIG. 13 is a diagram illustrating a display image in the command execution processing according to the modification example of the first embodiment. The display image is an image displayed on the display unit 101 of the display device 5 in a case where the distance d is the second threshold $d_2$ or above and smaller than the first threshold $d_1$. FIG. 13 will be described using the diagram (refer to FIG. 3) illustrating an image displayed on the display unit 101 of the display device 5 in a case where the practitioner's finger is arranged at a position corresponding to the position outside the B-mode image display region on the touch panel 42 (display unit 41). For example, in a case where the pointer 200 is positioned on the command image 103c, the control unit 39 performs setting such that the command image 103c and the command images (command images 103b and 103d) adjoining the command image 103c are set to be the command images as highlighting targets. According to the setting, the display image generation unit 33 generates an image highlighting the command images 103b to 103d as illustrated in FIG. 13.

Figure 14:
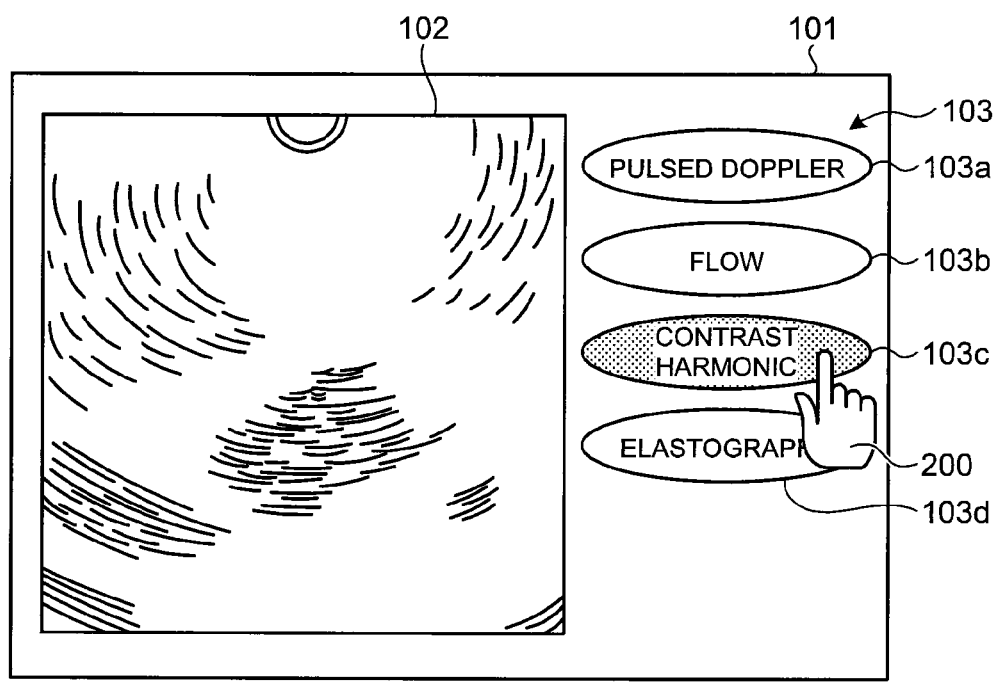
FIG. 14 is a diagram illustrating a display image in the command execution processing according to the modification example of the first embodiment of the present invention.

FIG. 14 is a diagram illustrating a display image in the command execution processing according to the modification example of the first embodiment. The display image is an image displayed on the display unit 101 of the display device 5 in a case where the distance d is smaller than the second threshold $d_2$. FIG. 14 will also be described using the diagram (refer to FIG. 3) illustrating an image displayed on the display unit 101 of the display device 5 in a case where the practitioner's finger is arranged at a position corresponding to the position outside the B-mode image display region on the touch panel (display unit 41). For example, in a case where the pointer 200 is positioned on the command image 103c, the control unit 39 performs setting such that the command image 103c is set to be the command image as a highlighting target. According to the setting, the display image generation unit 33 generates an image highlighting the command image 103c as illustrated in FIG. 14.

Back to the flowchart in FIG. 11, when a new detection signal from the detection sensor unit 43 is present (step S212: Yes), the control unit 47 returns to step S202 and repeats the above-described display processing. In contrast, when the new detection signal from the detection sensor unit 43 is absent (step S212: No), the control unit 47 proceeds to step S213.

In step S213, the control unit 47 judges whether an operation signal has been input from the touch panel 42. When the control unit 47 judges that the operation signal has not been input from the touch panel 42 (step S213: No), the control unit 47 returns to step S212 and repeats confirmation processing on the detection signal and the operation signal.

In contrast, when the control unit 47 judges that the operation signal has been input from the touch panel 42 (step S213: Yes), the control unit 47 outputs operating information according to the operation signal, to the control unit 39 (step S214).

On the ultrasound observation apparatus 3, the control unit 39 judges the presence or absence of input of operating information from the operation apparatus 4 (step S215). In a case where the control unit 39 judges that the operating information input is absent (step S215: No), the control unit 39 repeats confirmation of input of operating information. In contrast, in a case where the control unit 39 judges that the input of detection information is present (step S215: Yes), the control unit 39 proceeds to step S216.

In step S216, the execution command selection unit 36 determines the selected command image on the basis of input position coordinates on the touch panel 42 and the command image display position coordinates and selects a command corresponding to the selected command, as a command to execute. The execution command selection unit 36 outputs information related to the selected command, to the control unit 39. The control unit 39 performs control of execution of the selected command (step S217).

According to the above-described modification example, similarly to the above-described first embodiment, it is configured such that the executable command is selected and displayed on the display device 5 on the basis of the detected arrangement and shape of the finger and the practitioner's hand position with respect to the touch panel 42 (display unit 41), and that the command to execute is selected by touch operation on the touch panel 42. With this configuration, it is possible to perform input operation with high flexibility without removing eyes from the monitor (display unit 101). Moreover, according to the first embodiment, it is possible to select and execute a command while confirming the display unit 101. Accordingly, it is possible to achieve an effect of suppressing an error in operation.

According to the modification example, it is configured such that the command image is highlighted in accordance with the position of the practitioner's fingertip. Accordingly, it is possible to enhance visibility of the command image to select and possible to select a desired command image further reliably.

The modification example assumes that the operation signal is output in response to the contact of the practitioner's finger and/or thumb with the touch panel 42, and the execution command is selected in accordance with the position information (coordinate information) of the operation signal. Alternatively, however, it is allowable to configure such that the pointer 200 selects a command according to the command image to superpose (command image according to the position (coordinates) of the position of the practitioner's finger), as the execution command, in a case where the distance between the touch panel 42 (operation screen) and the practitioner's fingertip is a predetermined value (<the second threshold $d_2$) or below. It is allowable to configure to select a command corresponding to the command image 103c, as the execution command, in another exemplary case where the distance between the touch panel 42 and the practitioner's fingertip is a predetermined value (<the second threshold $d_2$) or below and the coordinate according to the position of the fingertip is the closest to the command image 103c, even when the touch position by the practitioner is not on the command image 103c.

Although the modification example assume the use of the first and the second thresholds, it is allowable to perform narrow-down display using any one of the thresholds.

Second Embodiment

Figure 15:
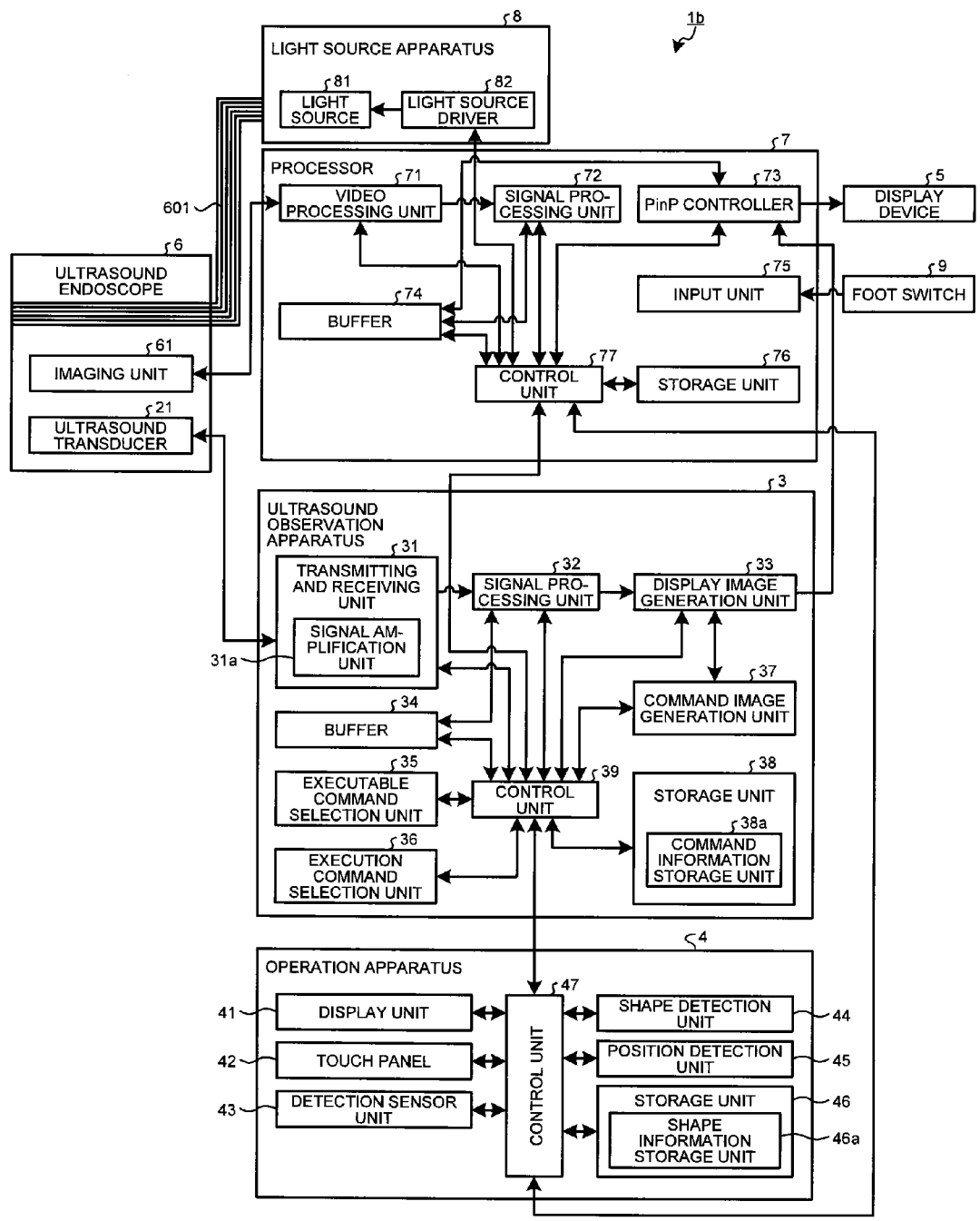
FIG. 15 is a block diagram illustrating a configuration of an ultrasound endoscope system according to a second embodiment of the present invention.
Figure 16:
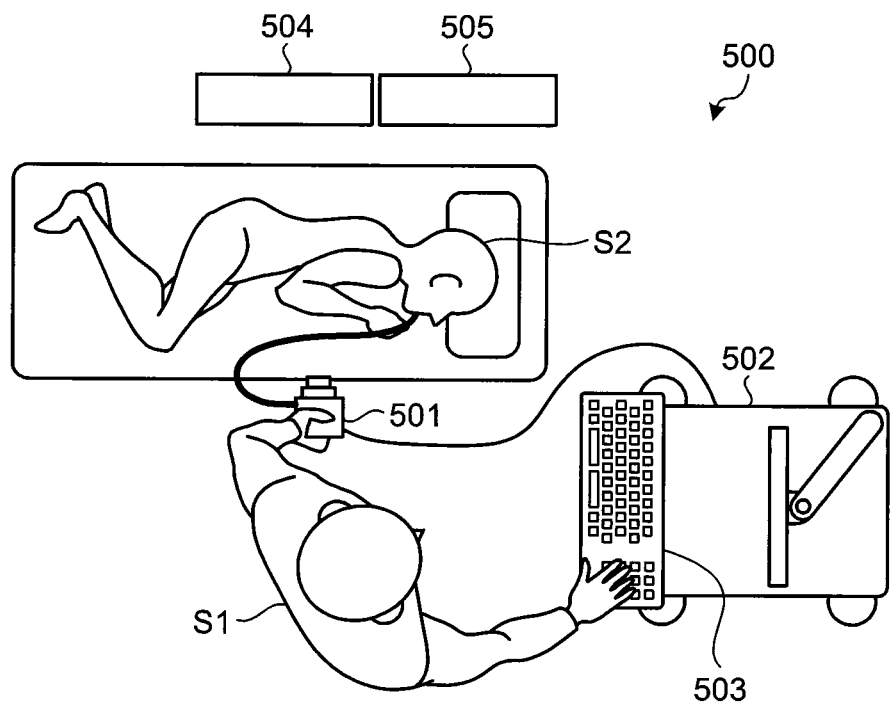
FIG. 16 is a schematic diagram illustrating a configuration of a system that performs conventional ultrasound diagnosis.

Next, a second embodiment of the present invention will be described. FIG. 15 is a block diagram illustrating a configuration of an ultrasound endoscope system according to the second embodiment. The reference signs are used to designate the same elements as those of the above embodiment. The above-described first embodiment describes the ultrasound diagnosis system that is an apparatus for observing an observation target using ultrasound, as an example. In contrast, the second embodiment will describe, an example, an ultrasound endoscope system as an ultrasound observation system equipped with an ultrasound endoscope including an ultrasound transducer for transmission and reception of the above-described ultrasound signals and an imaging element for imaging an optical region.

An ultrasound endoscope system 1b includes an ultrasound endoscope 6, an ultrasound observation apparatus 3, an operation apparatus 4, a processor 7, a display device 5, a light source apparatus 8, and an input unit (e.g. foot switch 9). The ultrasound endoscope 6 receives an ultrasound echo generated from an ultrasound pulse that is output and reflected, images an imaging region including the output region of the ultrasound pulse, and obtains an imaging signal as a result of the imaging. The ultrasound observation apparatus 3 generates an image based on the ultrasound echo obtained by the ultrasound endoscope 6. The operation apparatus 4 can simultaneously receive a plurality of sets of input instruction information, outputs the received information to the ultrasound observation apparatus 3 and operates the ultrasound observation apparatus 3. The processor 7 generates an image based on each of the ultrasound echo and the imaging signal, obtained by the ultrasound endoscope 6. The display device 5 displays various types of information including the ultrasound image data generated by the processor 7 and/or in-vivo image data. The light source apparatus 8 generates illumination light that is projected from the distal end of the ultrasound endoscope 6. The input apparatus (foot switch 9) is provided for inputting various instruction signals including the freeze instruction signal.

The ultrasound endoscope 6 includes, at its distal end, an imaging unit 61 and the ultrasound transducer 21. The imaging unit 61 is inserted into the body cavity of the subject and captures an in-vivo image of the subject. The ultrasound transducer 21 outputs an ultrasound pulse to an observation target and receives an ultrasound echo reflected from the observation target.

The imaging unit 61 is configured with an imaging element including two-dimensionally arranged pixels that generate imaging signals by receiving and photoelectrically converting the light. Exemplary imaging elements include an image sensor such as complementary metal oxide semiconductor (CMOS) and a charge coupled device (CCD).

The processor 7 includes a video processing unit 71, a signal processing unit 72, a picture-in-picture (PinP) controller 73, a buffer 74, an input unit 75, a storage unit 76, and a control unit 77.

The video processing unit 71 transmits and receives electrical signal with the imaging unit 61. The video processing unit 71 is electrically connected with the imaging unit 61, transmits imaging conditions such as imaging timing to the imaging unit 61 and receives an imaging signal generated by the imaging unit 61.

The signal processing unit 72 generates in-vivo image data to be displayed by the display device 5, on the basis of the imaging signal received by the video processing unit 71. The signal processing unit 72 executes predetermined image processing toward the imaging signal, thereby generating in-vivo image data including in-vivo images. The in-vivo image (observation image) is a color image that includes values of R, G, and B, that is, variables when the RGB color system is employed as a color space.

The signal processing unit 72 sequentially performs signal processing toward the imaging signals output from the video processing unit 71 so as to generate in-vivo image data, and outputs the generated in-vivo image data to the buffer 74. In a case where a freeze instruction signal for the in-vivo image is input by pressing of the foot switch 9, for example, the signal processing unit 72 extracts the in-vivo image data from the buffer 74 and outputs the extracted in-vivo image to the PinP controller 73, as a frozen image.

The PinP controller 73 obtains the in-vivo image data stored in the buffer 74 and performs, toward the obtained in-vivo image data, predetermined processing such as data decimation and gradation processing corresponding to the data step size determined in accordance with the image display range on the display device 5, and thereafter, outputs the processed signal as display-oriented in-vivo image data (image data of the normal observation mode). Furthermore, the PinP controller 73 performs control of simultaneously displaying the display-oriented in-vivo image data and the B-mode image data (image data of the ultrasound observation mode) transmitted from the ultrasound observation apparatus 3, on the display device 5. For example, the PinP controller 73 generates display image data for displaying a B-mode image with a size smaller than an in-vivo image, on the in-vivo image or around the in-vivo image, performs display control of the generated display image data, performs live display of the in-vivo image or the B-mode image onto the display device 5, while performing display control of displaying a frozen image selected by a freeze instruction, among the in-vivo image and the B-mode image, onto the display device 5.

The buffer 74 is performed with a ring buffer, for example, and stores, along the timeline, a fixed amount (a predetermined number of frames) of in-vivo image data generated by the signal processing unit 72. When the capacity is insufficient (when the predetermined number of frames of in-vivo image data are stored), a predetermined number of frames of the latest in-vivo images are stored along the timeline by overwriting the oldest in-vivo image data with the latest in-vivo image data.

The input unit 75 receives input of an operation instruction signal from input apparatuses such as the foot switch 9, a trackball keyboard, and outputs the operation instruction signal to the control unit 77. In a case where the foot switch 9 is pressed and the operation instruction signal is input, for example, the input unit 75 outputs an instruction signal including a function, such as a freeze instruction, allocated to the foot switch 9, to the control unit 77.

The storage unit 76 stores various programs for operating the ultrasound endoscope system 1b, data including various parameters needed for operation of the ultrasound endoscope system 1b, or the like. The storage unit 76 also stores various programs including an operation program for executing a method for operating the processor 7 and the ultrasound endoscope system 1b. The operation programs can be recorded in a computer-readable recording medium such as a hard disk, flash memory, CD-ROM, DVD-ROM, flexible disk, or the like, and can be distributed broadly. It is also possible to obtain the above-described various programs by downloading them via a communication network.

Herein, the communication network refers to one implemented by, for example, a known public network, a local area network (LAN), a wide area network (WAN), regardless of wired or wireless.

The above-configured storage unit 76 is implemented using a read only memory (ROM) in which various programs are pre-installed, a random access memory (RAM) that stores calculation parameters and data for each of processing, or the like.

The control unit 77 includes a central processing unit (CPU) having control functions, various calculation circuits. The control unit 77 reads, from the storage unit 76, information stored in the storage unit 76, and executes various types of calculation processing related to the method for operating the ultrasound endoscope system 1b including the ultrasound observation apparatus 3, thereby integrally controlling the ultrasound endoscope system 1b.

The light source apparatus 8 includes a light source 81 and a light source driver 82.

The light source 81 includes a light source that projects illumination light and one or more lenses, and projects light (illumination light) by drive of the light source under control of the light source driver 82. The illumination light generated by the light source 81 is transmitted through a light guide 601 and projected from the distal end of the ultrasound endoscope 6 onto the subject.

Under the control of the control unit 77, the light source driver 82 supplies current to the light source 81, thereby projecting the illumination light. The control unit 77 controls drive of the light source driver 82, thereby controlling the amount of power supplied to the light source 81 and controlling the drive timing of the light source 81.

The foot switch 9 includes a bar that receives input of a signal when the bar is stepped on by a foot. Stepping-on operation toward the bar by the practitioner causes the foot switch 9 to receive input of operation related to the freeze instruction of an image, and outputs an operation signal to the input unit 75.

In the second embodiment, the PinP controller 73 performs control for displaying ultrasound image data (including command image) according to the first embodiment and the modification example described above, and for displaying the in-vivo image data imaged by the imaging unit 61, onto the display device 5. The command execution processing may also be command executing processing in the ultrasound observation mode such as in the above-described first embodiment and the modification example, or may be command executing processing in the normal observation mode. In the case of the normal observation mode, as similarly to the above-described display unit 101, it is configured to provide an in-vivo image display unit for displaying an in-vivo image and provide an information display section that is arranged in a region different from the in-vivo image display unit and from the above-described display unit 101 and that is capable of displaying various types of information such as command images, and executable commands are selected and displayed by arrangement of practitioner's finger.

As commands in the normal observation mode in a case where the practitioner's finger is arranged on the in-vivo image display unit, the commands may include the comment input mode, the cursor input mode, an in-vivo image enlargement mode/reduction mode, the distance measurement mode in the in-vivo image. As commands in the normal observation mode in a case where the practitioner's finger is arranged on the information display section, the commands may include a live display image mode, and a frozen image display mode. It is also allowable to configure such that a signal as a trigger to switch over between the normal observation mode and the ultrasound observation mode is output by pressing the foot switch 9 or output by pressing the button provided on an operating unit (not illustrated) on the ultrasound endoscope 6.

Also in the normal observation mode, it is possible to select executable commands and select execution commands by operation on the touch panel 42, in accordance with the flowchart illustrated in the above-described first embodiment and the modification example. For example, in step S102 in the flowchart illustrated in FIG. 2, the shape detection unit 44 and the position detection unit 45 detect arrangement and shape of the finger and a practitioner's hand position with respect to the touch panel 42 (display unit 41) on the basis of the detection signal, and the control unit 39 performs determination of the observation mode, and the executable command selection unit 35 selects, in step S105, an executable command in accordance with the arrangement, the shape, and the position of the finger, and the observation mode. Note that execution command selection using the touch panel 42 may be replaced by the selection by pressing the foot switch 9 and the selection using the button of the operating unit of the ultrasound endoscope 6.

According to the above-described second embodiment, similarly to the above-described first embodiment, it is configured such that the executable command is selected and displayed on the display device 5 on the basis of the detected arrangement and shape of the finger, and on practitioner's hand position with respect to the touch panel 42 (display unit 41), and that the command to execute is selected by touch operation on the touch panel 42. With this configuration, it is possible to perform input operation with high flexibility without removing eyes from the monitor (display unit 101). Moreover, according to the second embodiment, it is possible to select and execute a command while confirming the display unit 101. Accordingly, it is possible to achieve an effect of suppressing an error in operation.

Note that while the second embodiment assumes that the display device 5 and the foot switch 9 are connected on the processor 7 side, they may be connected on the ultrasound observation apparatus 3, or may be connected with both the processor 7 and the ultrasound observation apparatus 3.

Moreover, while the second embodiment assumes that PinP controller 73 is provided on the processor 7, it may be provided on the ultrasound observation apparatus 3.

Moreover, while the second embodiment assumes the ultrasound observation system using an endoscope, it is also possible to apply an ultrasound observation system including a fixed-point camera for capturing an observation region and the above-described ultrasound diagnosis systems 1 and 1a.

For example, while the above-described first and second embodiments and the modification example assume that the observation target is a living tissue, it is also applicable to an industrial endoscope for observing characteristics of a material. The observation apparatus according to the present invention is applicable both to external and internal portions of the body. It is also allowable to configure such that observation target signals are transmitted and received not only with projection of ultrasound but also with projection of infrared rays.

While the above-described first and second embodiments and modification example assume that executable commands are selected independently of the practitioner (operator), it is also possible to register an executable command for each of the operators, in the storage unit 38, or the like, and thus to select the executable command corresponding to each of the operators and to perform command selection processing according to individual operation. It is also allowable to configure such that the shape (pattern) of the finger is stored in the storage unit 38, or the like, for each of the observation modes, and mode switching is performed for the shape of the finger. For example, it is allowable to perform display mode switching between, for example, displaying an ultrasound image alone and displaying in-vivo images alone, on the display unit of the display device 5, in accordance with the shape of the finger.

The above-described first and second embodiments and modification example assume that the surface (contact surface) of the touch panel 42 (display unit 41) is used as an operation screen and the spatial position of the practitioner's finger is detected with respect to the operation screen. The configuration, however, is not limited to this. It would be sufficient that a predetermined surface (for example, an upper surface of a console) is used as the operation screen and positional relationship between the spatial position (coordinates) of the practitioner's finger with respect to the operation screen and the position (coordinates) of the image displayed by the display device 5 is detected in association with each other, by the detection unit.

According to some embodiments, it is possible to perform input operation with high flexibility without removing eyes from the monitor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical diagnosis apparatus configured to obtain a signal for generating an image of an observation target and configured to cause an external display to display an observation image based on the obtained signal to perform diagnosis, the medical diagnosis apparatus comprising:
   a detection unit including a sensor that receives light reflected from a finger of a practitioner and converts the received light to a detection signal, the detection unit being configured to produce a signal pattern in accordance with the detection signal, to detect a shape of the finger of the practitioner by matching the signal pattern with previously acquired signal patterns, and to detect a spatial position of the finger of the practitioner in accordance with the detection signal; and
   a processor comprising hardware, the processor being configured to:
      select one or more commands executable by the medical diagnosis apparatus in accordance with the shape and the spatial position of the finger of the practitioner detected by the detection unit;
      generate a command image corresponding to the selected one or more commands and generate a finger shape image indicating the shape of the finger of the practitioner; and
      generate a display image using the generated command image, the finger shape image and the observation image.

2. The medical diagnosis apparatus according to claim 1, wherein the processor is further configured to select an execution target command in accordance with the spatial position of the finger of the practitioner and a display position of the command image.

3. The medical diagnosis apparatus according to claim 2, wherein the processor is further configured to select the execution target command in accordance with a relative positional relationship between the spatial position of the finger of the practitioner and the display position of the command image if the minimum distance is a predetermined value or below.

4. The medical diagnosis apparatus according to claim 2, further comprising:
   a display configured to display the observation image and the command image; and
   a touch panel disposed on a display screen of the display and having a contact surface with which the finger of the practitioner is configured to come in contact, the touch panel being configured to receive input corresponding to a contact position of the finger of the practitioner.

5. The medical diagnosis apparatus according to claim 4, wherein the processor is further configured to select the execution target command in accordance with the contact position of the finger of the practitioner received by the touch panel, and with the display position of the command image.

6. The medical diagnosis apparatus according to claim 1, wherein the detection unit is configured to further detect a minimum distance between a predetermined operation screen and the finger of the practitioner.

7. The medical diagnosis apparatus according to claim 6, wherein the processor is further configured to generate the display image that highlights at least the command image corresponding to the position of the finger of the practitioner if the minimum distance detected by the detection unit is smaller than a threshold related to the minimum distance.

8. The medical diagnosis apparatus according to claim 7, wherein the processor is further configured to:
   generate, as the display image, a first display image that highlights the command image corresponding to the position of the finger of the practitioner and a second command image spatially adjoining the command image if the minimum distance is smaller than the threshold and equal to or greater than a second threshold that is smaller than the threshold; and
   generate, as the display image, a second display image that highlights the command image corresponding to the position of the finger of the practitioner if the minimum distance is smaller than the second threshold.

9. The medical diagnosis apparatus according to claim 1, wherein the processor is further configured to select one or more executable commands in accordance with the shape and the spatial position of the finger of the practitioner, and with an operation mode.

10. The medical diagnosis apparatus according to claim 1, wherein the processor is further configured to generate, as the display image, one of: a first display image in which the command image is superposed on the observation image in accordance with the spatial position of the finger of the practitioner; and a second display image in which the command image and the observation image are arranged side by side.

11. The medical diagnosis apparatus according to claim 1, further comprising a memory configured to store a plurality of commands executable by the processor, and the shape and the spatial position of the finger of the practitioner so as to be associated with one another.

12. The medical diagnosis apparatus according to claim 11, wherein the memory stores, for each practitioner, the one or more commands to be selected by the processor.

13. An ultrasound observation system comprising:
an ultrasound transducer configured to transmit ultrasound to an observation target and to generate an echo signal being an electrical signal converted from an ultrasound echo that is generated from the ultrasound transmitted to the observation target and reflected from the observation target;
an imaging sensor configured to generate an imaging signal being an electrical signal converted from a received light signal;
a display configured to display a plurality of observation images based on at least one of the echo signal and the imaging signal;
a detection unit including a sensor that receives light reflected from a finger of a practitioner and converts the received light to a detection signal, the detection unit being configured to produce a signal pattern in accordance with the detection signal, to detect a shape of the finger of the practitioner by matching the signal pattern with previously acquired signal patterns, and to detect a spatial position of the finger of the practitioner in accordance with the detection signal; and
a processor comprising hardware, the processor being configured to:
select one or more executable commands in accordance with the shape and the spatial position of the finger of the practitioner detected by the detection unit;
generate a command image corresponding to the selected one or more commands and generate a finger shape image indicating the shape of the finger of the practitioner; and
generate a display image using the generated command image, the finger shape image and the observation image.

14. A method for operating a medical diagnosis apparatus, the medical diagnosis apparatus being configured to obtain a signal for generating an image of an observation target and configured to cause an external display to display an observation image based on the obtained signal to perform diagnosis, the method comprising:
detecting a shape of a finger of a practitioner and a spatial position of the finger of the practitioner;
selecting one or more commands executable by the medical diagnosis apparatus in accordance with the shape and the spatial position of the finger of the practitioner;
generating a command image corresponding to the selected one or more commands and generating a finger shape image indicating the shape of the finger of the practitioner; and
generating a display image using the generated command image, the finger shape image and the observation image.

15. A non-transitory computer-readable recording medium with an executable program stored thereon for operating a medical diagnosis apparatus, the medical diagnosis apparatus being configured to obtain a signal for generating an image of an observation target and configured to cause an external display to display an observation image based on the obtained signal to perform diagnosis, the program causing the medical diagnosis apparatus to execute:
detecting a shape of a finger of a practitioner and a spatial position of the finger of the practitioner;
selecting one or more commands executable by the medical diagnosis apparatus in accordance with the shape and the spatial position of the finger of the practitioner;
generating a command image corresponding to the selected one or more commands and generating a finger shape image indicating the shape of the finger of the practitioner; and
generating a display image using the generated command image, the finger shape image and the observation image.

* * * * *